US011264987B2

(12) United States Patent
Cheng et al.

(10) Patent No.: US 11,264,987 B2
(45) Date of Patent: Mar. 1, 2022

(54) LIVING BODY DETECTION METHOD AND APPARATUS

(71) Applicant: Vicwood Prosperity Technology Limited, Hong Kong (HK)

(72) Inventors: Ka Wai Eric Cheng, Hong Kong (HK); Man Yau Law, Hong Kong (HK); Hin Hung Ng, Hong Kong (HK); Kwok Shing Wong, Hong Kong (HK)

(73) Assignee: Vicwood Prosperity Technology Limited, Hong Kong (HK)

( * ) Notice: Subject to any disclaimer, the term of this patent is extended or adjusted under 35 U.S.C. 154(b) by 110 days.

(21) Appl. No.: 16/761,267

(22) PCT Filed: Nov. 5, 2018

(86) PCT No.: PCT/IB2018/058653
§ 371 (c)(1),
(2) Date: May 4, 2020

(87) PCT Pub. No.: WO2019/087154
PCT Pub. Date: May 9, 2019

(65) Prior Publication Data
US 2021/0409022 A1 Dec. 30, 2021

(30) Foreign Application Priority Data
Nov. 3, 2017 (HK) .................. 17111337.0

(51) Int. Cl.
*H03K 17/96* (2006.01)
*G08B 21/22* (2006.01)
(Continued)

(52) U.S. Cl.
CPC ....... *H03K 17/9645* (2013.01); *A61B 5/0531* (2013.01); *G08B 21/22* (2013.01); *H02H 5/12* (2013.01)

(58) Field of Classification Search
CPC .. H03K 17/9645; A61B 5/0531; G08B 21/22; H02H 5/12
(Continued)

(56) References Cited

U.S. PATENT DOCUMENTS

2004/0215853 A1* 10/2004 Marx .................... H03K 17/96
710/69

FOREIGN PATENT DOCUMENTS

| CN | 1544959 A | 11/2004 |
| CN | 102859875 A | 1/2013 |

(Continued)

OTHER PUBLICATIONS

The Extended European Search Report for European Patent Application No. 18874374.4 dated Nov. 9, 2020.
(Continued)

*Primary Examiner* — Tomi Skibinski

(57) ABSTRACT

Methods and apparatus for detecting possible living body contact at an electrical contact surface is disclosed, comprising sending a non-hazardous probing signal to the contact surface, detecting an electrical response from the contact surface in response to the electrical probing signal, and determining whether a captured responsive signal has characteristics of an expected responsive pulse, and to output a positive output signal indicative of possible living body to mitigate risks of electrical shock.

20 Claims, 15 Drawing Sheets

(51) Int. Cl.
*A61B 5/0531* (2021.01)
*H02H 5/12* (2006.01)

(58) Field of Classification Search
USPC .......................................................... 327/517
See application file for complete search history.

(56) References Cited

FOREIGN PATENT DOCUMENTS

| CN | 203314960 U | 12/2013 |
|----|-------------|---------|
| CN | 107157481 A | 9/2017 |
| WO | 2011132129 A1 | 10/2011 |
| WO | 2016174644 A1 | 11/2016 |
| WO | 2018083637 A1 | 5/2018 |

OTHER PUBLICATIONS

Abedellah Ouazani et al.: "The Electric Impedance of the Human Body", Oct. 7, 2013, XP055464494, URL: http://psrcentre.org/images/extraimages/7%201013005.pdf.

International Search Report for PCT/IB2018/058653 dated Feb. 27, 2019.

* cited by examiner

Fig. 1
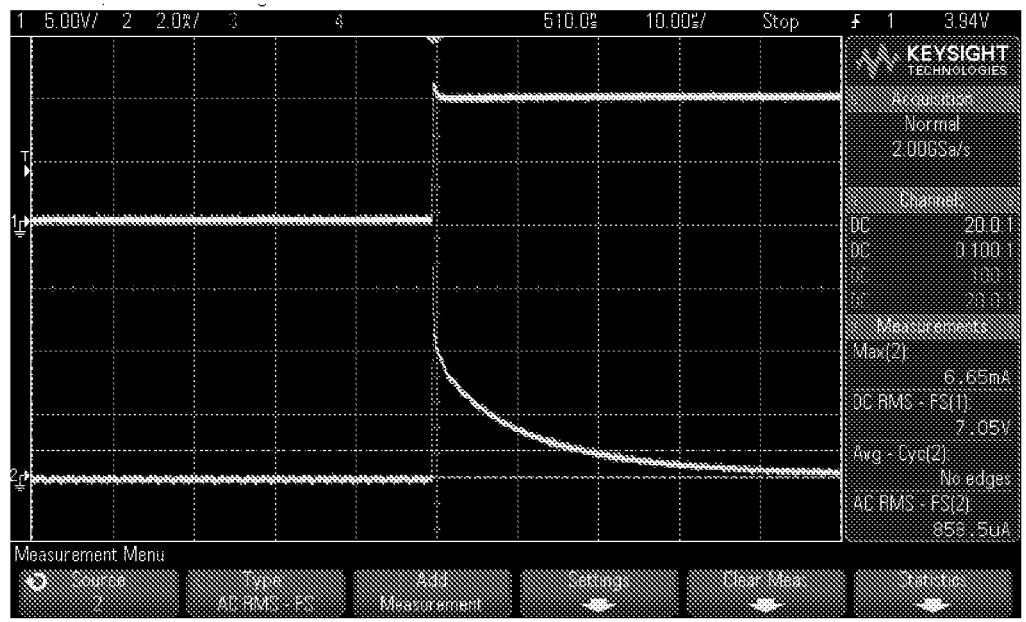
Fig. 2A1
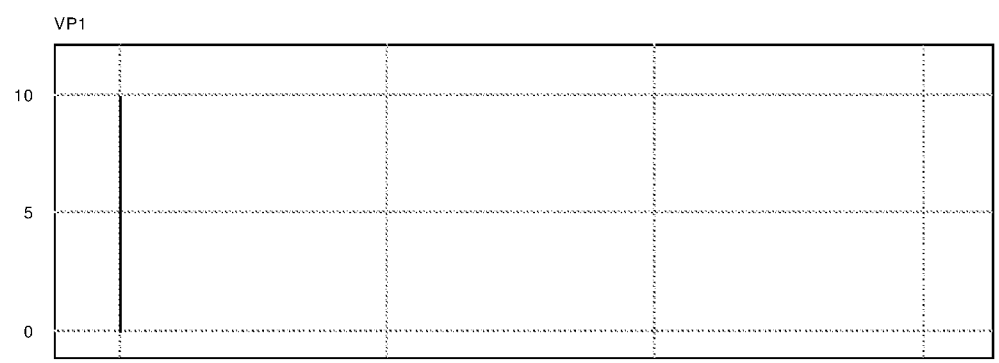
Fig. 2A2
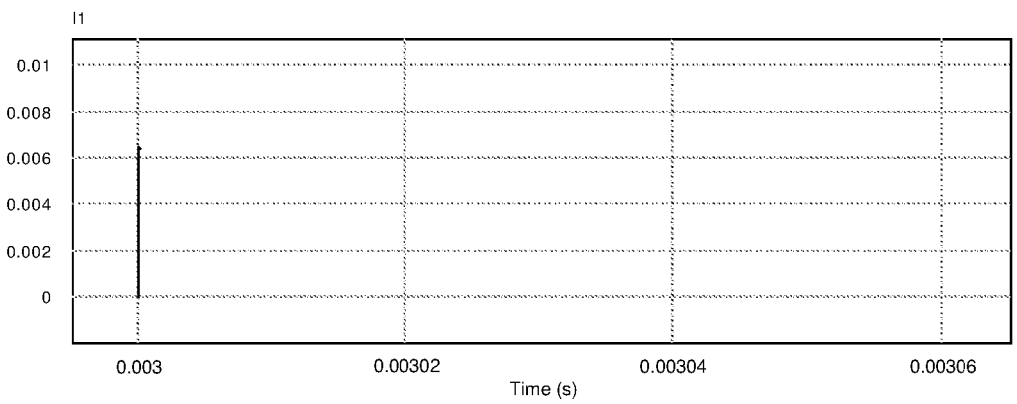

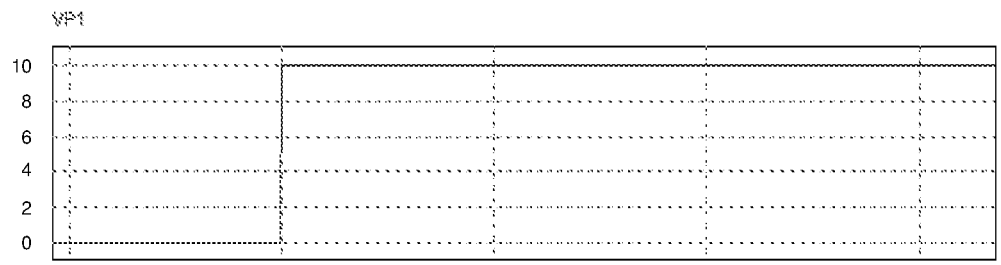
Fig. 2B1
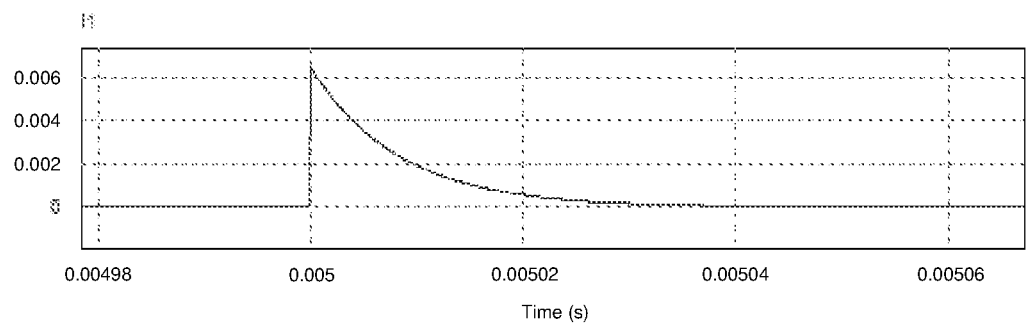
Fig. 2B2
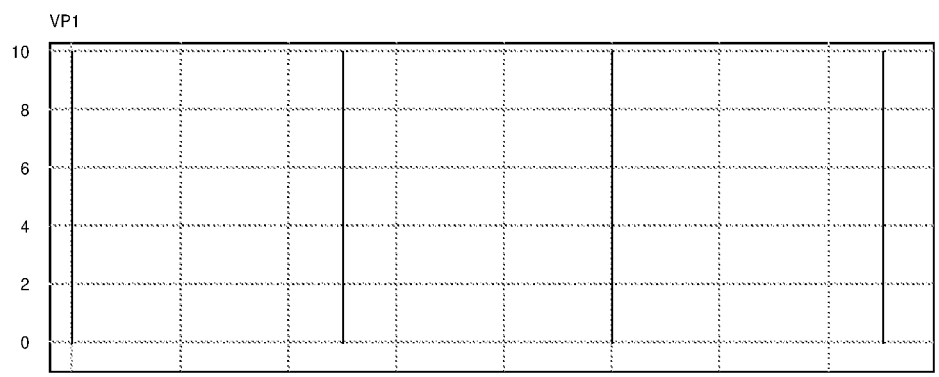
Fig. 2C1
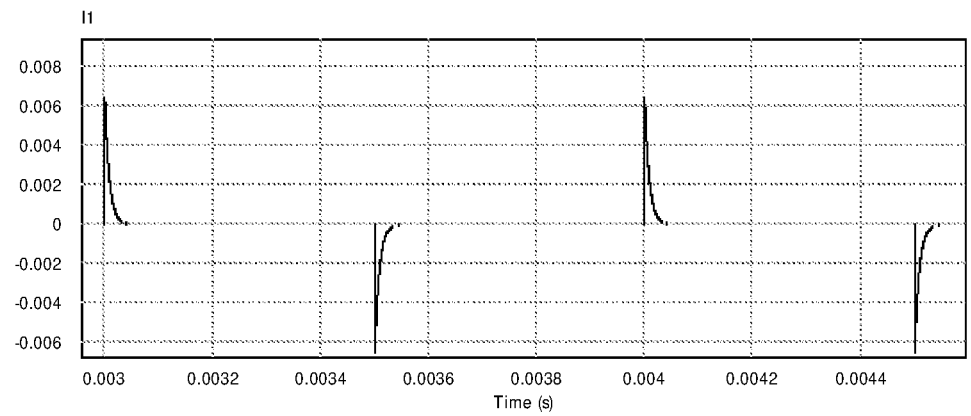
Fig. 2C2

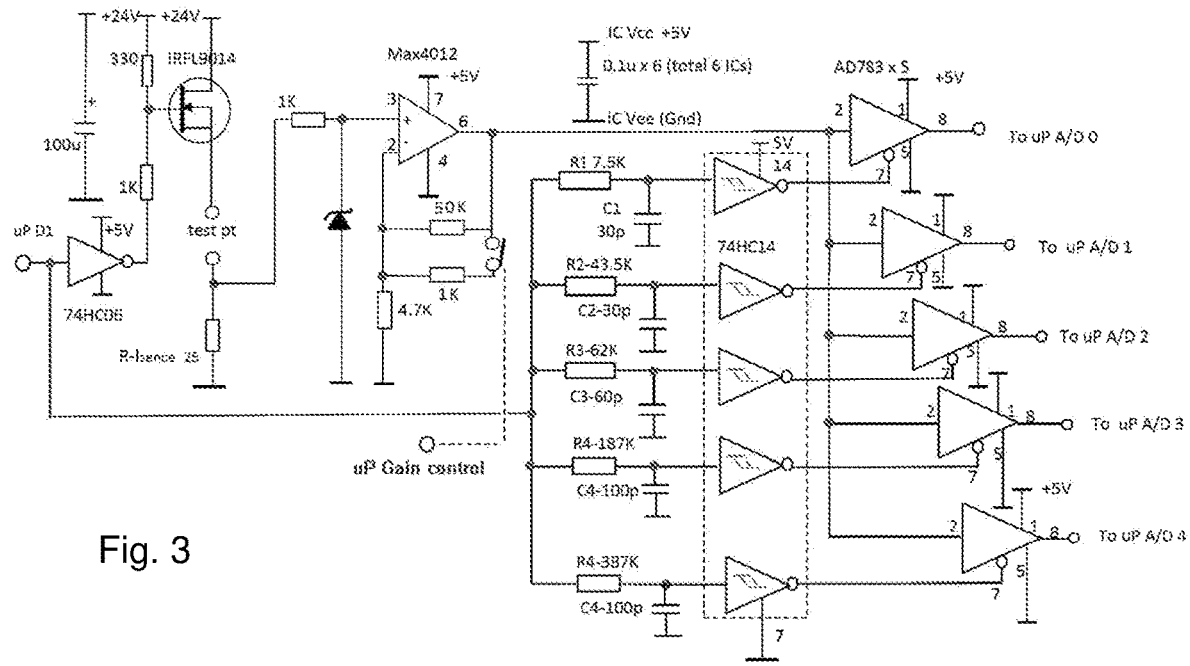
Fig. 3
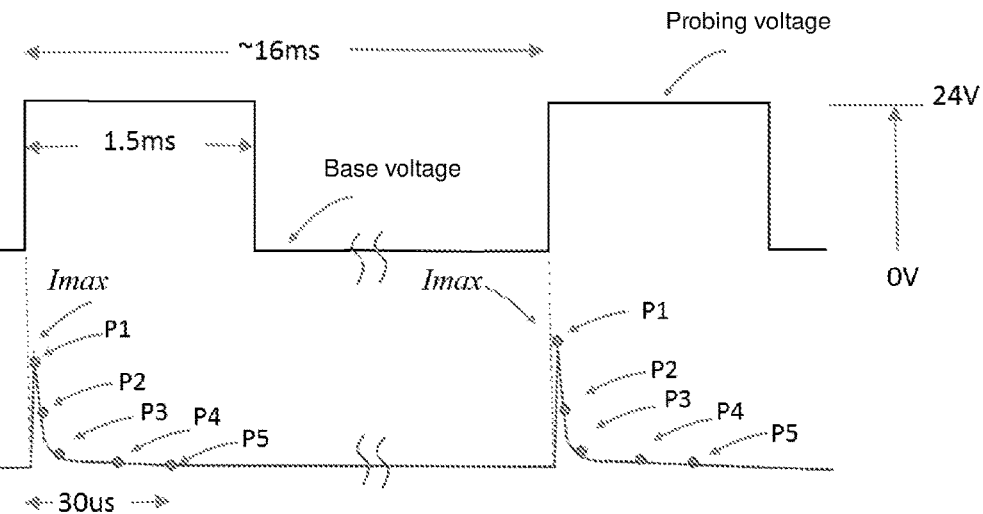
Fig. 3A1
Fig. 3A2

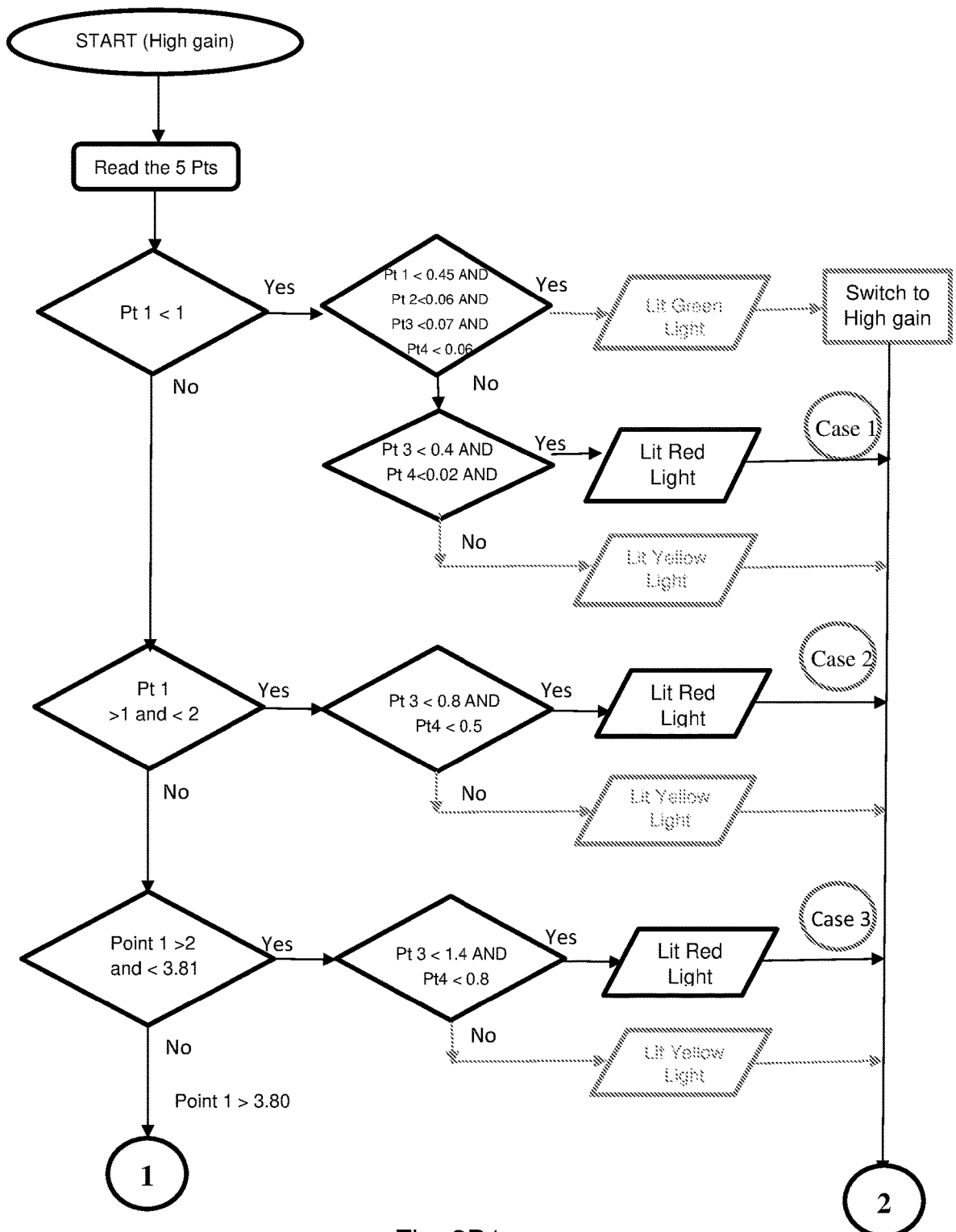
Fig. 3B1

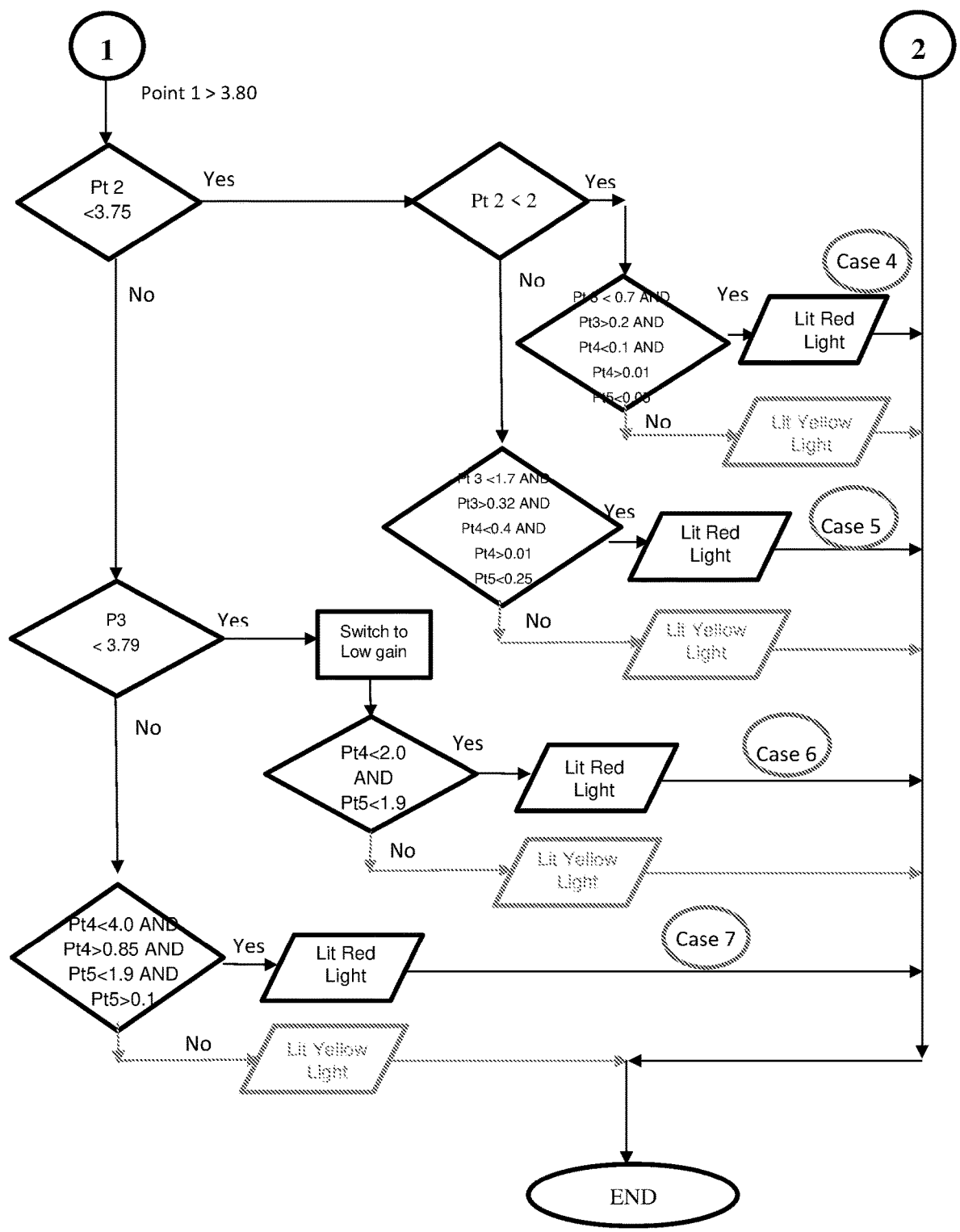
Fig. 3B2

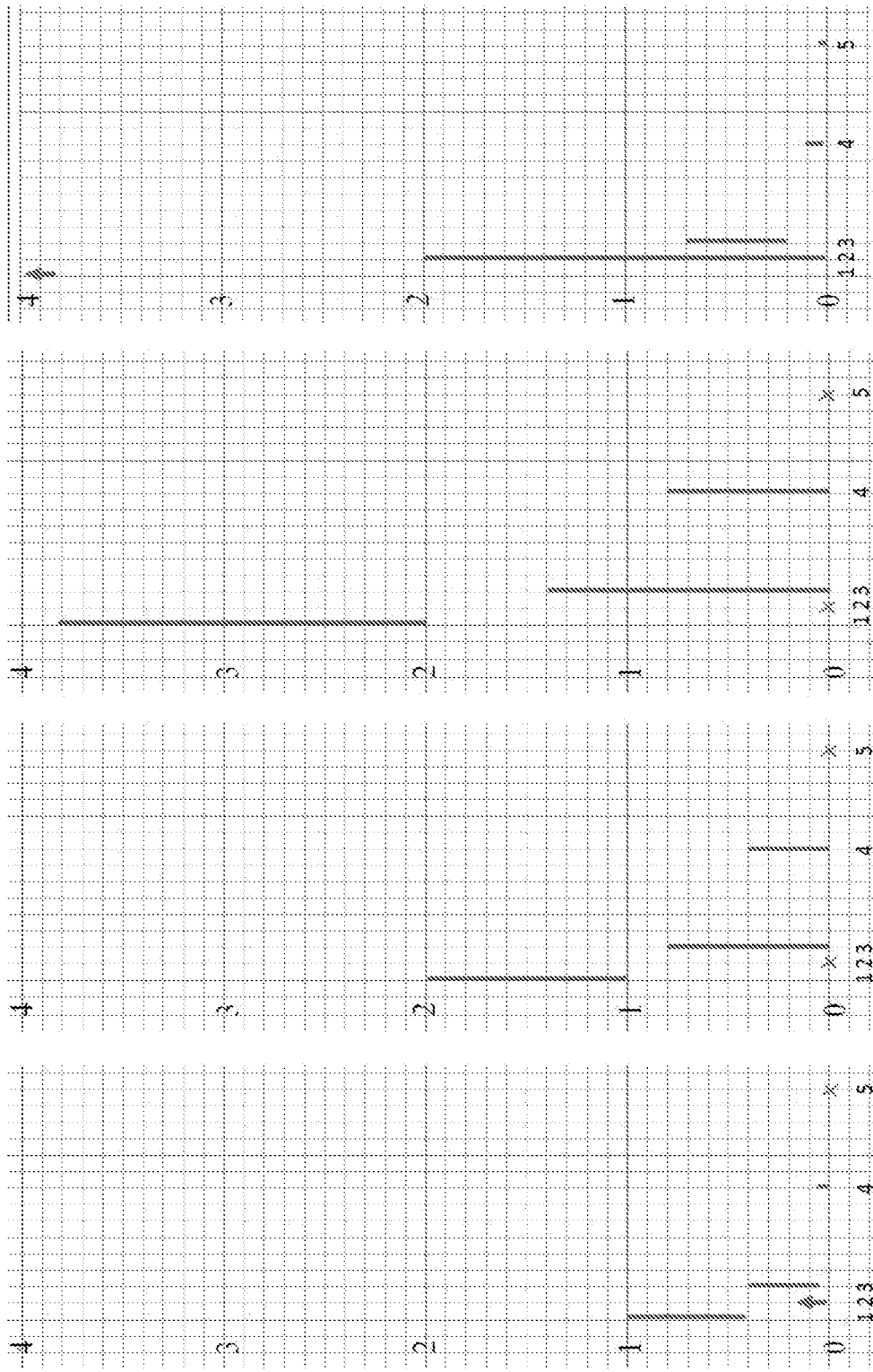

Figure 5A:
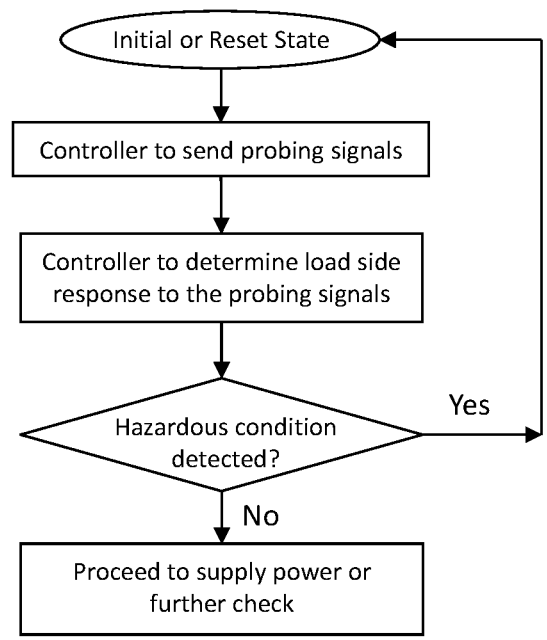
Figure 5B:
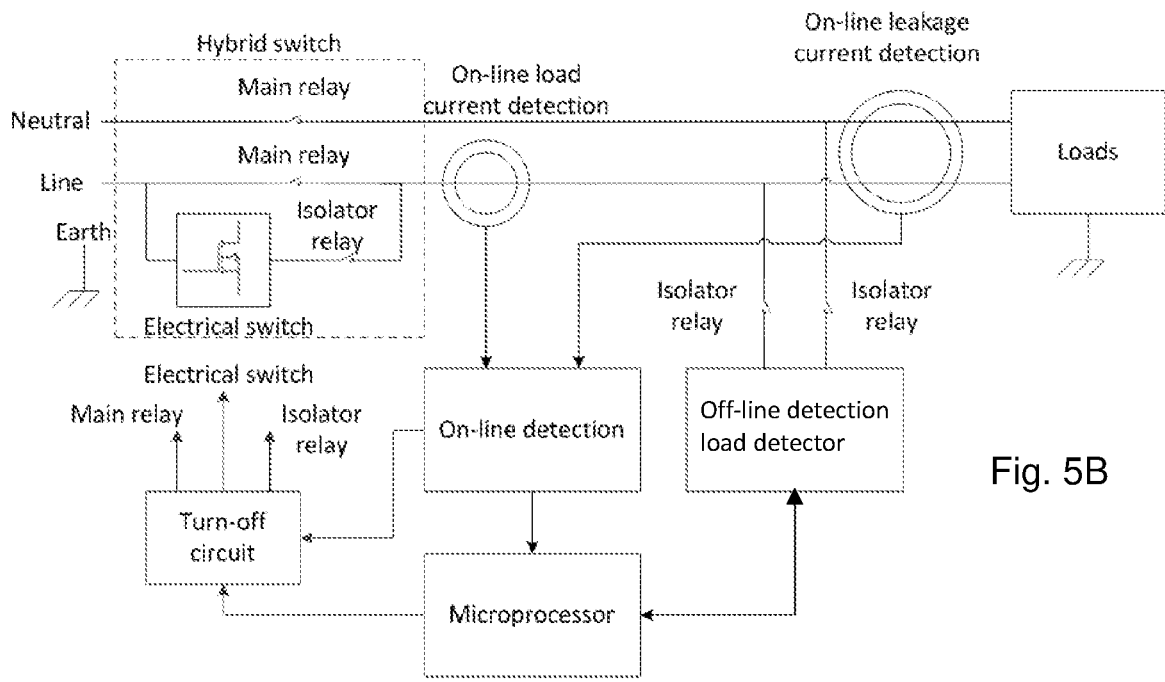
Figure 6:
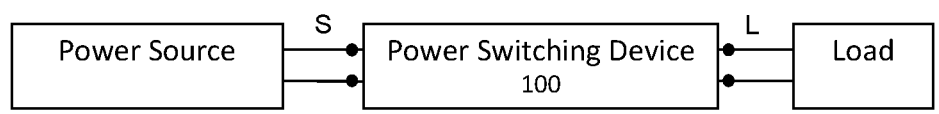

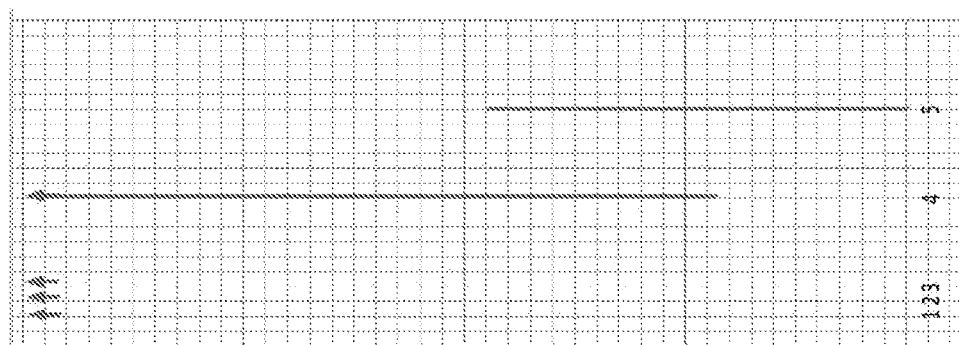
Fig. 3C7
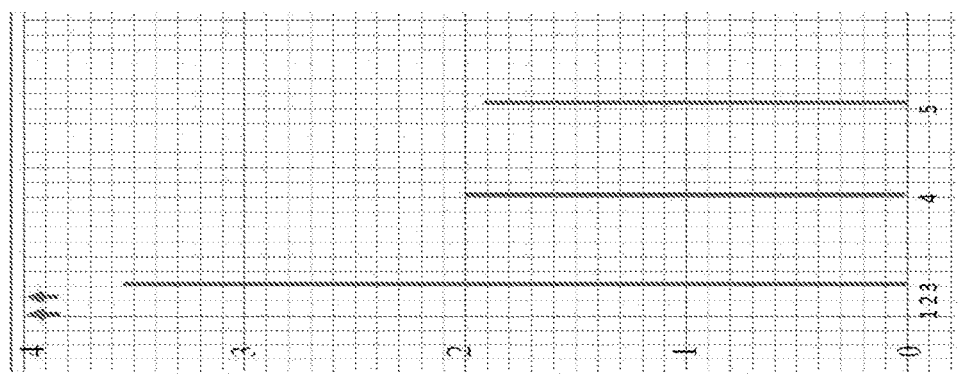
Fig. 3C6
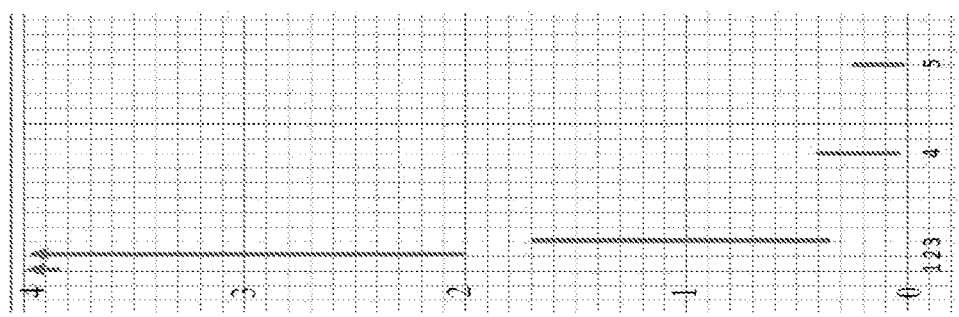
Fig. 3C5
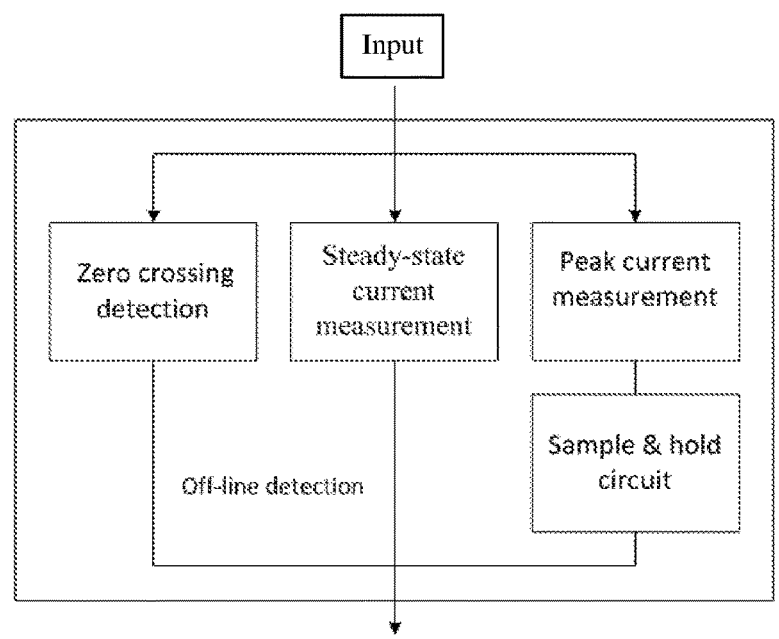
Fig. 4

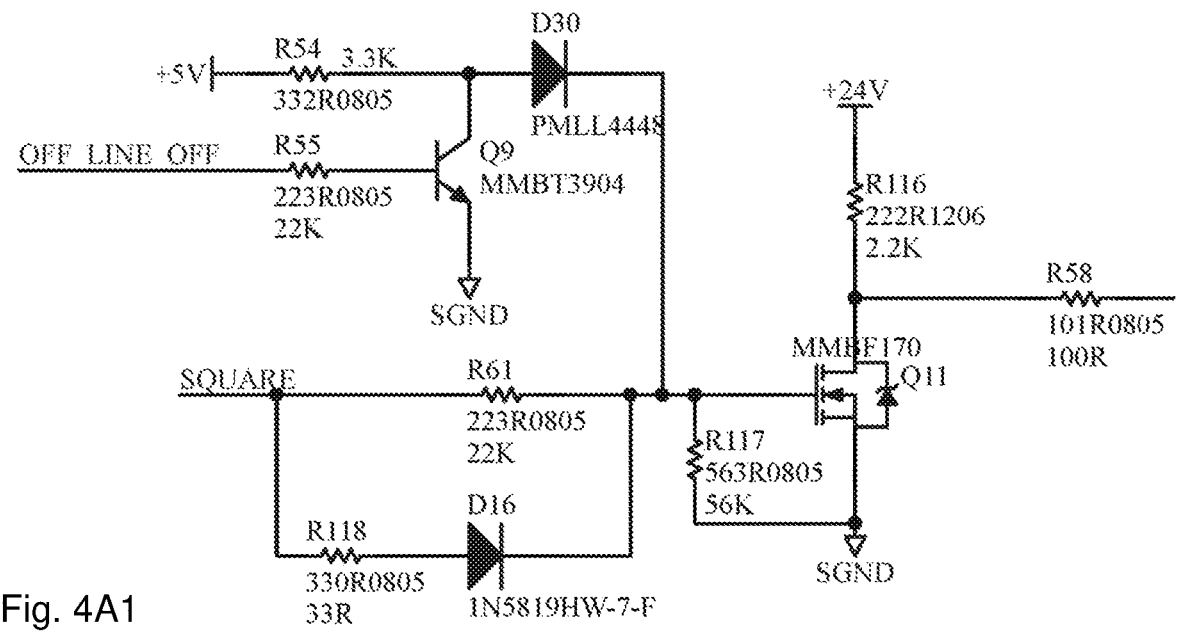
Fig. 4A1
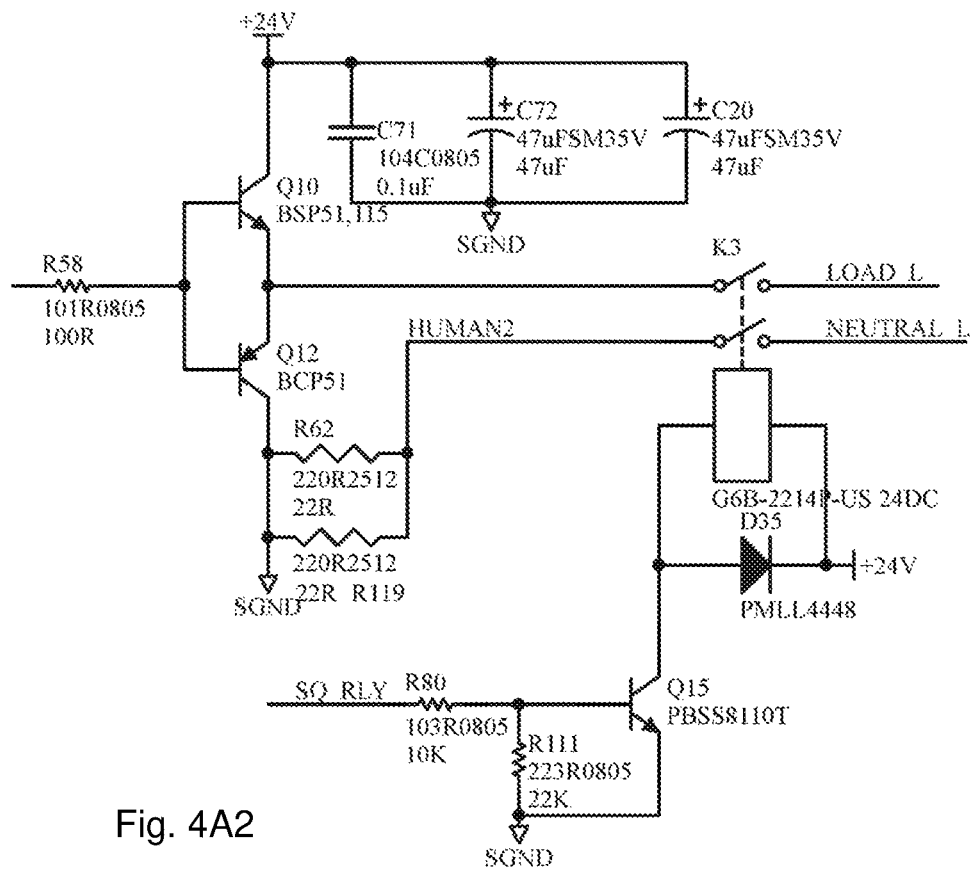
Fig. 4A2

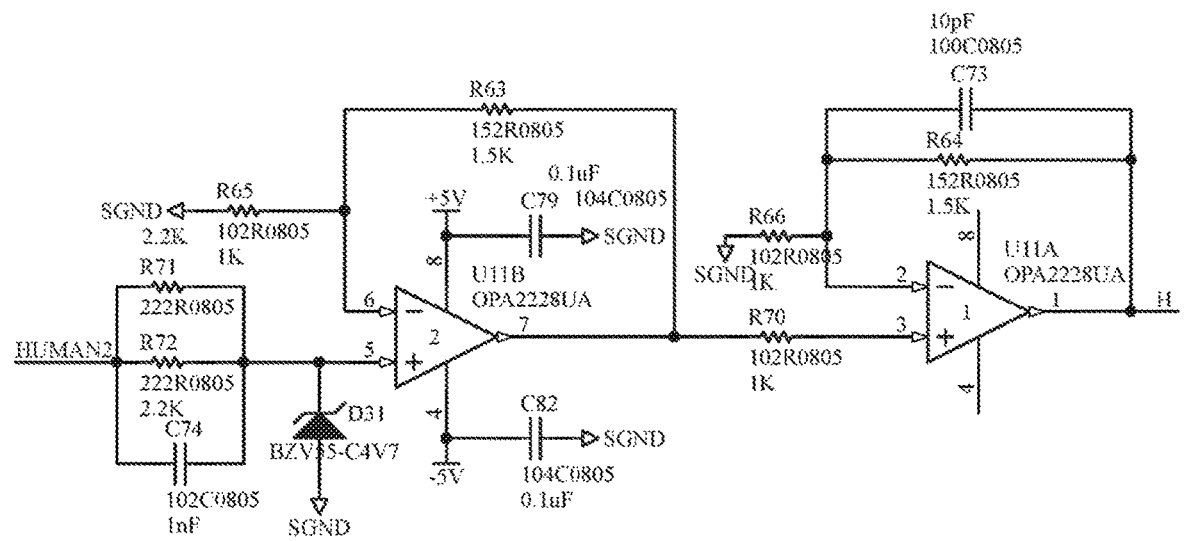
Fig. 4B1
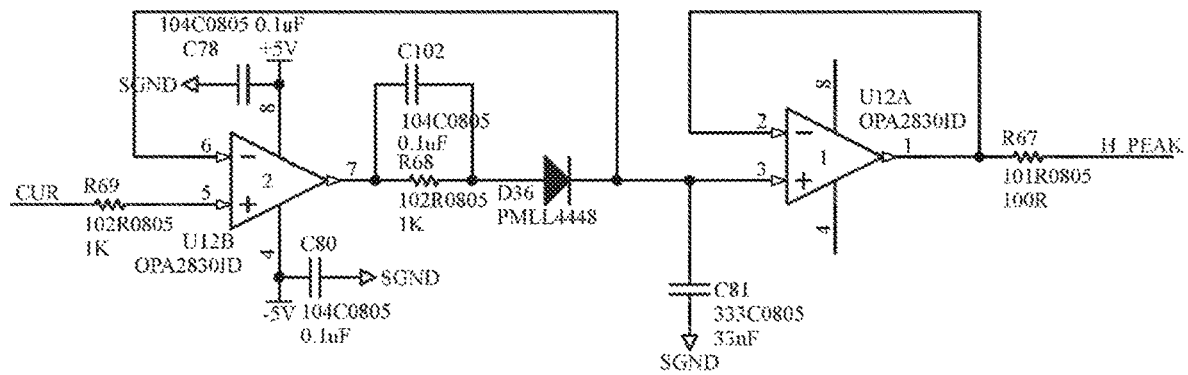
Fig. 4B2

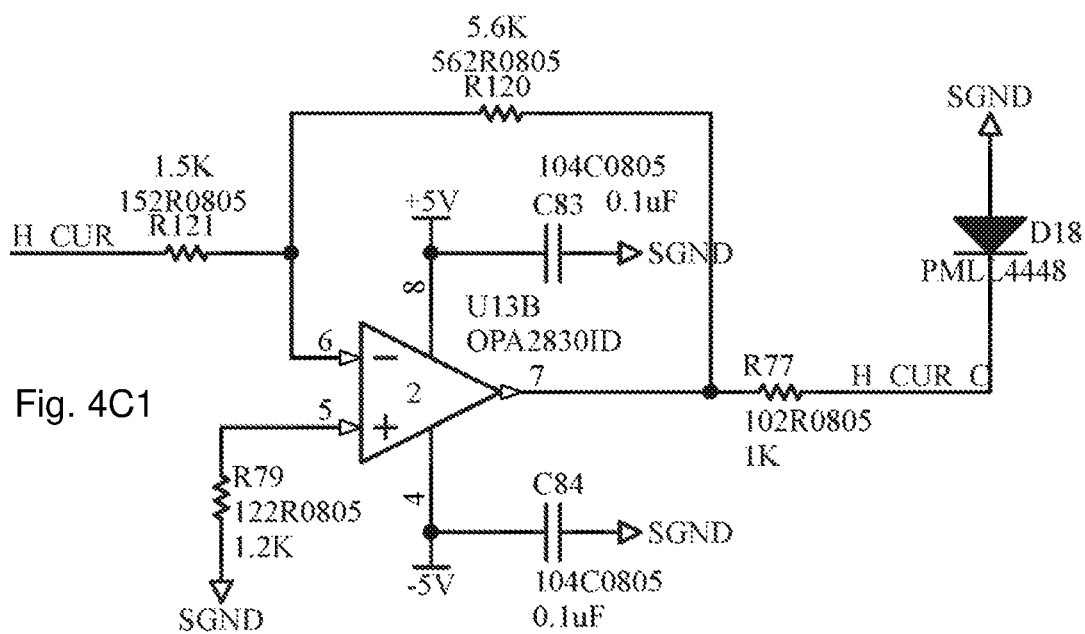
Fig. 4C1
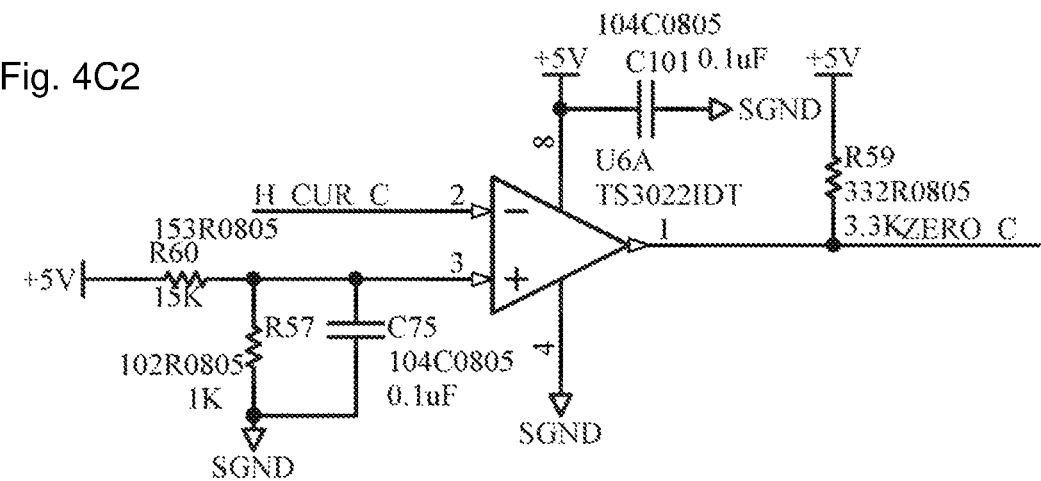
Fig. 4C2
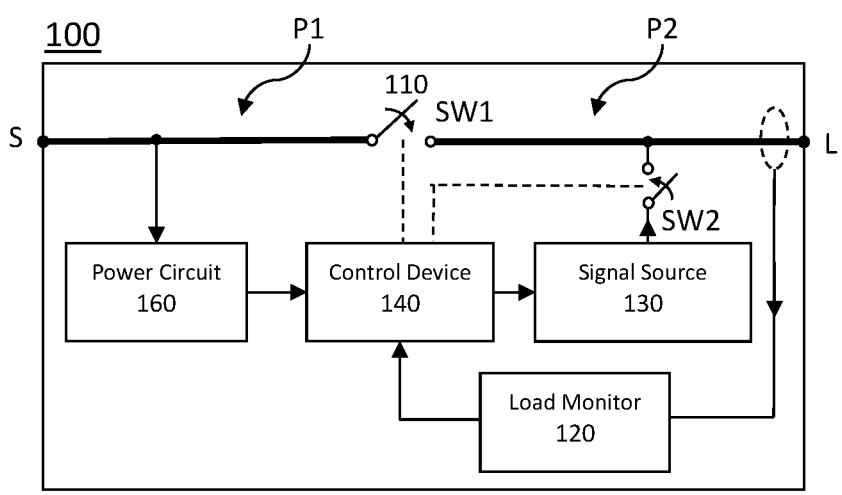
Fig. 5

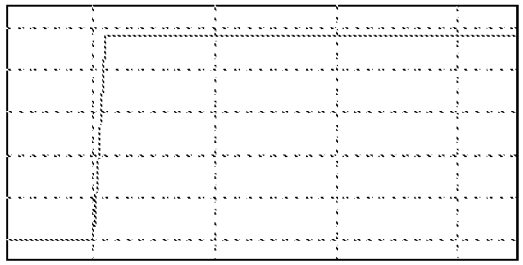
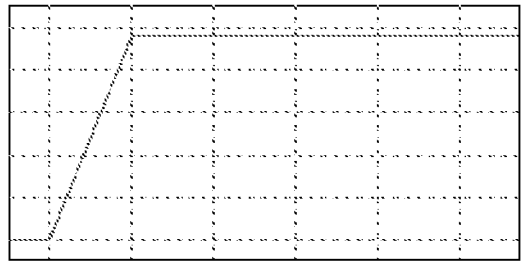
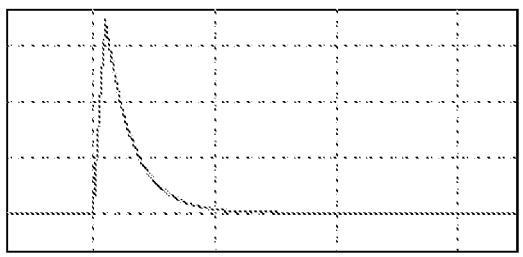
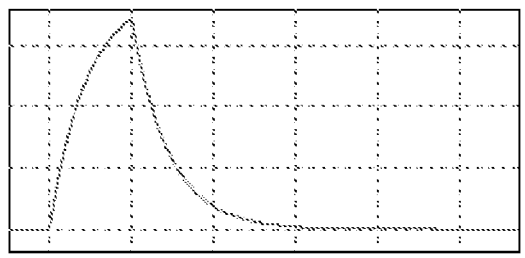
Fig. 10A
Fig. 10B
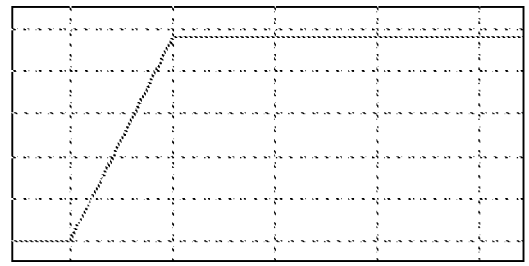
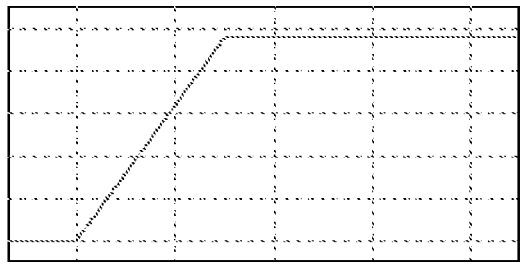
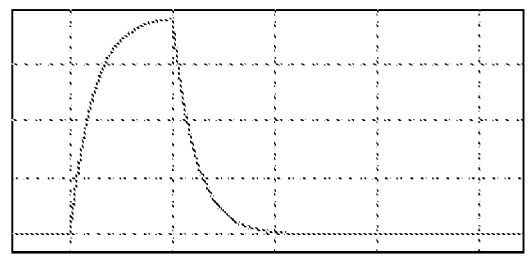
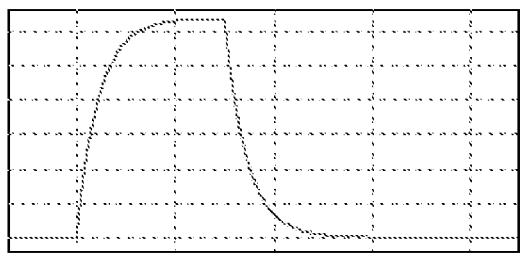
Fig. 10C
Fig. 10D

LIVING BODY DETECTION METHOD AND APPARATUS

FIELD

The present disclosure relates to methods and apparatus for detecting living body contact at a contact surface, and to methods and apparatus for controlling power supply to mitigate risks of electrical shock.

BACKGROUND

Electricity is a form of energy that is present almost everywhere in modern livings. However, the human body and other living bodies are somewhat conductive and electrical current passing through a human body can cause electric shock and be fatal.

Studies have shown that different parts of the human body can be regarded as forming a circuit comprising distributed resistive (R) and capacitive (C) components, and the values of impedances of the resistive (R) and capacitive (C) components depend on a number of factors such as the current path, the touch voltage, the duration of current flow, the current frequency, the degree of moisture of the skin, the surface area of contact, the pressure exerted and the temperature. From arm-to-arm or arm-to-leg, the resistance is typically between 1 kΩ to 1MΩ, but the resistance can drop to 100Ω with punctured skin.

Below are some typical threshold values when a current of 15-100 Hz passes through a human body:

| | |
|---|---|
| 1 mA | Threshold of perception |
| 5 mA | noticeable shock, involuntary movement |
| 10 mA | Let-go threshold |
| 30 mA | Possible ventricular fibrillation |
| 50 mA | probable |
| 100 mA | respiratory arrest, fibrillation, death becoming likely |
| 1 A | Nerve damage, burns, death likely |

Ventricular fibrillation is known to be the main cause of fatal electric shock accidents in the frequency range of 15 Hz to 100 Hz, and 50 Hz and 60 Hz are of course the standard mains supply frequency.

It is desirable to provide means or measures to mitigate risks of fatal electrical shocks.

DISCLOSURE

Electric currents are essential for operations of vital human organs such as the heart and the brain. However, an electric current having an amplitude of current and a flow duration exceeding a safe limit can be hazardous and can cause injuries or death by electrocution.

A living person can feel an electric current if the current flowing through the person reaches a magnitude known as a threshold of perception. The threshold of perception depends on several parameters, such as the area of body contact ("contact area"), the conditions of contact (dry, wet, pressure, temperature), and also on physiological characteristics of the individual. The threshold of perception for an AC (alternating current) current of 50/60 Hz is typically between 0.25 mA to 1 mA when the current. The DC (direct current) threshold of perception is about four times the AC threshold of perception.

Electric current can cause a person to lose muscular control if the current flowing through the person reaches a magnitude known as a "let-go" threshold. When this happens, the would not be able to control his/her muscle to move away from an electrified contract surface until the currents flow stops. The let-go threshold depends on several parameters, such as the contact area, the shape and size of the electrodes and also on the physiological characteristics of the person. The let-go threshold for an AC (alternating current) current of 50/60 Hz is typically taken as about 10 mA and there is no definable let-go threshold for DC.

Electric current can cause ventricular fibrillation if the current flowing through the person reaches a magnitude known as a threshold of ventricular fibrillation. Ventricular fibrillation is considered to be the main cause of death by electrical shock, although there is also some evidence of death due to asphyxia or cardiac arrest. The threshold of ventricular fibrillation depends on physiological parameters, such as anatomy of the body, state of cardiac function, etc., as well as on electrical parameters, such as duration and pathway of current flow, current parameters, etc. For shock durations by AC currents below 100 millisecond (ms), ventricular fibrillation may occur at a current magnitude above 500 mA. For shock durations longer than the cardiac cycle, the threshold of fibrillation for DC is several times higher than for AC. For shock durations shorter than 200 ms, the threshold of fibrillation is approximately the same as for AC measured in root-mean-square (rms) values.

The human body permits flow of electric current and can be considered as a passive network comprising resistive and capacitive components in so far as studies of electrical shock are concerned.

The human body can be regarded as a passive impedance network comprising a first skin impedance ($Z_{p1}$), a second skin impedance ($Z_{p2}$) and an internal impedance ($Z_i$) for studies of electrical safety. The first skin impedance ($Z_{p1}$), the second skin impedance ($Z_{p2}$) and the internal impedance ($Z_i$) are electrically connected in series, with the internal impedance electrically ($Z_i$) interconnecting and intermediate the first and second skin impedances. The total impedance ($Z_T$) of the human body is equal to $Z_{p1}+Z_i+Z_{p2}$.

The internal impedance of the human body has impedance characteristics of a parallel connection of a resistive component and a capacitive component, and can be represented by an equivalent circuit of an impedance network comprising an internal resistor $R_i$ and an RC (resistor and capacitor) branch connected in parallel. The RC branch consists of a second internal resistor and an internal capacitor $C_i$ connected in series (Source: (source: British standard document PD6519-1:1995, FIG. 1). The value of the internal impedance ($Z_i$) depends primarily on the current path and, to a lesser extent, on the surface area of the contact. Experiments show that the internal capacitance $C_i$ has a value of several picofarad (pF).

The skin impedance of the human body has impedance characteristics of a parallel connection of a resistive component and a capacitive component, and can be represented by an equivalent circuit of an impedance network comprising a resistor having a skin resistance $R_{pi}$ and a capacitor having a skin capacitance $C_{pi}$ connected in parallel, where i=1 or 2. Studies show that the skin resistance $R_{pi}$ has a value of several hundred kohm (kΩ). (source: British standard document PD6519-1:1995).

The value of the skin impedance ($Z_{p1}$, $Z_{p2}$) depends on the voltage, frequency, duration of the current flow, surface area of contact, pressure of contact, the degree of moisture of the skin, temperature and type of the skin. For touch voltages up to approximately 50 V AC, the value of the impedance of the skin of a person varies widely with surface area of contact, temperature, perspiration, rapid respiration, and other factors. For higher touch voltages over approximately 50 V, the skin impedance decreases considerably and becomes negligible when the skin breaks down. The skin impedance falls when the current is increased. (source: British standard document PD6519-1:1995)

A living human body appears to have the electrical properties and characteristics of a passive impedance network which is resistive and capacitive and can be represented as such a network in so far as electrical shock safety studies and solutions are concerned. However, the values of the various resistive and capacitive elements forming the network appear to be non-constant and non-linear and vary widely according to many factors and parameters, such as contact area, current path(s), conditions of contact (dry, wet, pressure, temperature) and physiological parameters of the living body and characterization of the human bodies without complicated algorithms is difficult, if not impossible. However, it is found that the impedances of human bodies are within a predictable range.

For example, the values of total body impedance $Z_T$ with a hand to hand current path and large contact area (5,000 square mm (mm²) to 10,000 square mm) for an example touch voltage of 10V and example frequencies from 25 Hz to 20 kHz and measured using 10 living human body samples fall from a maximum impedance at the low frequency end to a minimum impedance at the high frequency end. The maximum impedance at the low frequency end (25 Hz in the example) has an average value of about 5.3 k$\Omega$ or 5.4 k$\Omega$ and a variation of about 3 k$\Omega$, or about 1.5 k$\Omega$ onboth sides of the average. The minimum impedance at the high frequency end (20 kHz in the example) was found to have an average value of about 900$\Omega$ and a variation of about 80$\Omega$-100$\Omega$, or 40$\Omega$-50$\Omega$ on both sides of the average. The total body impedance $Z_T$ decreases rapidly from the maximum impedance value at the low frequency end to stabilize asymptotically at about 5 kHz to 10 kHz. The change in total body impedance $Z_T$ at 10 kHz or above is found to be small and in the 40$\Omega$-50$\Omega$ range (source: British standard document PD6519-1:1995, FIG. 6).

For example, the values of total body impedance $Z_T$ with a hand to hand current path and large contact areas (5,000 square mm (mm²) to 10,000 square mm) for an example touch voltage of 25V and example frequencies from 25 Hz to 2 kHz and measured using 10 living human body samples fall from a maximum impedance at the low frequency end to a minimum impedance at the high frequency end. The maximum impedance at the low frequency end (25 Hz in the example) has an average value of about 3.23 k$\Omega$ or 3.3 k$\Omega$. The minimum impedance at the high frequency end (2 kHz in the example) was found to have an average value of about 700$\Omega$. The total body impedance $Z_T$ decreases rapidly from a maximum impedance value at the low frequency end to stabilize asymptotically at about 2 kHz (source: British standard document PD6519-1:1995, FIG. 7).

For example, the total body impedance of a population for a percentile rank of 50% for touch voltages from 10V to 1000V AC and a frequency range from 50 Hz to 2 kHz for a current path hand to hand or hand to foot varies between about 5.5 k$\Omega$ at 10V AC 50 Hz and about 1.1 k$\Omega$ at 1 kV AC 50 Hz. The total body impedance for touch voltages at or above 50V AC all converge to approach an asymptotic value of about 650$\Omega$ at about 2 kHz (source: British standard document PD6519-1:1995, FIG. 8).

For example, the values of total body impedance $Z_T$ with a hand to hand current path at AC 50/60 Hz for large contact areas at 25V is between 1750$\Omega$ (5% of population) and 6100$\Omega$ (95% of population), with 50% of population at 3250$\Omega$; at 50V is between 1450$\Omega$ (5% of population) and 4375$\Omega$ (95% of population), with 50% of population at 2625$\Omega$; at 75V is between 1250$\Omega$ (5% of population) and 2200$\Omega$ (95% of population), with 50% of population at 3500$\Omega$; and at 100V isbetween 1200$\Omega$ (5% of population) and 3500$\Omega$ (95% of population), with 50% of population at 1875$\Omega$ (source: British standard document PD6519-1:1995, Table 1).

When a living person touches a contact surface which has a surface voltage so that there is a voltage difference or a potential difference between the living person and the contact surface, a current will flow through the body of the living person ("living body" in short). For example, when a living person touches a contact surface which is at an elevated voltage or a positive voltage above the voltage of the living body, a current will from the contact surface into the living body due to the voltage difference or potential difference between the living body and the conduct surface. Conversely, when a living person touches a contact surface which is at a depressed voltage or a negative voltage below the voltage of the living body, a current will from the living body into the contact surface. While the descriptions herein are with reference to a contact surface having an elevated voltage with respect to a living body, it should be understood that the descriptions, terms and features shall apply mutatis mutandis to the condition where the contact surface is at a depressed voltage with respect to the voltage of a living body without loss of generality. A contact surface herein means an electrical conductive contact surface which permits flow of electrical current and a current herein means electrical current without loss of generality.

Experiments and measurements show that when a living body touches a contact surface which is at a constant voltage or a DC voltage elevated above the voltage of the living body, there is an inrush of current (or "current inrush" in short) that flows into the living body at the instant or moment when the living body is in direct electrical contact with the contact surface. The current inrush occurs almost immediately or instantaneously in response to the contact surface touching and the current that flows into the living body follows a substantially regular pattern of rising to a current peak within a very short rise time and then falls from the current peak to a steady state current level after a fall time which is substantially longer than the rise time. The aforesaid substantially regular pattern that the responsive current rising to a current peak within a very short rise time and then falls from the current peak to a steady state current level after a fall time which is substantially longer than the rise time is repeatable and is believed to represent a characteristic electrical response profile of a living body when touching a contact surface which is at an elevated constant voltage or a DC voltage. The inrush current is in the form of an asymmetrical current pulse having a current magnitude profile which is non-symmetrical about the current peak in the time domain, with the current peak at or very close to the time domain origin, that is, the time domain zero.

Experiments and measurements show that it is possible to determine whether there is living body contact at a contact surface by sending a non-hazardous probing signal to the contact surface and evaluating responsive signals coming from the contact surface in response to the probing signal. In devising a suitable probing signal, it is noted that the touching of a contact surface which is at an elevated voltage level by a living person is effectively equivalent to the application of a step voltage pulse having a voltage amplitude equal to the elevated voltage level as a touch voltage to the human body.

According to the disclosure, an electronic circuit arrangement for detection, as well as methods for detection, of electrical contact of a living body with a contact surface is disclosed. The living body has electrical characteristics resembling an impedance network comprising a first impedance portion, a second impedance portion and a third impedance portion connected in series. The first impedance portion comprises a first capacitor of a first capacitance value and a first resistor of a first resistance value connected in parallel to form a first impedance bridge, the second impedance portion comprises a second capacitor of a second capacitance value and a second resistor of a second resistance value connected in parallel to form a second impedance bridge, and the third impedance portion comprises a third capacitor of a third capacitance value and a third resistor of a third resistance value connected in parallel to form a third impedance bridge; and the impedance network has a characteristic charge rise-time and a characteristic discharge fall-time.

In some embodiments, the electronic circuit arrangement comprises a solid-state controller, a non-volatile data storage device, a probing signal source and a responsive signal collector. The signal source is to generate a probing pulse or a train of probing pulses as a probing signal, and to transmit the probing signal to the contact terminals. The responsive signal collector is for collecting a responsive signal at the contact terminals, the responsive signals being signals generated in response to or in reaction to the probing signal acting on the contact terminals. The probing pulse comprises a probing pulse base state at a probing pulse base state voltage, a probing state at a probing state voltage and a probing pulse intermediate state having intermediate voltages. The probing pulse rises from the base state voltage to the probing state voltage in a rise-time which is a probing pulse rise time, stays in the probing pulse probate state for a duration which defines a probing state duration, returns to the probing pulse base state at the end of the probing state, and stays in the probing pulse base state for a probing base state duration until end of the probing pulse. The intermediate voltages of the probing pulse intermediate state increase with time when the probing pulse changes from the probing pulse base state to the probing state.

The probing pulse and the impedance network are related or characterized such that when the probing pulse is applied on the impedance network, an expected response pulse comprising an expected pulse base having an expected pulse base magnitude and pertinent electrical characteristics is expected. The pertinent electrical characteristics comprises an expected pulse peak, an expected pulse steady state and an expected pulse transition state interconnecting the expected pulse peak and the expected pulse steady state. The expected pulse peak has an expected pulse signal magnitude, the expected pulse peak signal magnitude being an electrical parameter bearing or having a correlation between the probing state voltage and the second resistance value. The expected pulse steady state has an expected steady state signal magnitude, the steady state signal magnitude bearing or having a correlation between the probing state voltage and sum of resistance values of the resistors of the impedance network; and the expected pulse transition state has a fall time or fall-time characteristics commensurate with or corresponding to the characteristic discharge fall-time of the impedance network; and the controller is to capture a plurality of electrical parameters of the responsive signal at a plurality of capture times, to determine with reference to the captured electrical parameters whether the responsive signal comprises a response pulse having the pertinent electrical characteristics of or corresponding to the expected response pulse, and to send out a control signal indicative of positive living body detection upon a positive outcome of determination.

In some embodiments, the probing pulse is configured such that the expected pulse peak is a single dominant peak of the expected response pulse and having an expected peak magnitude of a first electrical polarity. The steady state signal magnitude of the expected pulse steady state has a non-zero magnitude and the first electrical polarity, and the expected response pulse is a non-zero-crossing pulse.

In some embodiments, the probing pulse is configured such that the expected steady state signal magnitude is intermediate the expected pulse peak signal magnitude and the expected pulse base magnitude, and the expected steady state signal magnitude, the expected pulse peak signal magnitude and the expected pulse base magnitude have same electrical polarity which is the first electrical polarity.

In some embodiments, the probing pulse is configured such that the expected response pulse rises from the expected pulse base to the expected pulse peak in an expected pulse rise time, and the expected pulse rise time is equal to or slightly larger than the probing pulse rise time.

In some embodiments, the probing pulse is configured such that the expected response pulse falls from the expected pulse peak to the expected pulse steady state in an expected pulse fall time, and the expected pulse fall time is equal to or shorter than the probing state duration of the probing pulse.

In some embodiments, the probing pulse is configured such that the expected response pulse begins to fall from the expected pulse steady state towards the expected pulse base state at a time when the probing pulses falls from the probing state to the base state, and the reaches the expected pulse base state during the probing pulse base state of a probing pulse.

In some embodiments, the probing pulse is configured such that the expected response pulse has a rising side and a rising portion and a falling side and a falling portion, the rising side and the falling side are divided by the expected pulse peak, and the rising portion and the falling portion are interconnected by the expected pulse peak. The rising portion has a rising portion duration and the falling portion has a falling portion duration, the rising portion is a thin portion and the falling portion is a slowly flaring fat portion, and the falling portion duration is significantly longer than the rising portion duration.

In some embodiments, the expected pulse transition state and the expected pulse steady state are on the falling side and occur sequentially after the expected response pulse has risen to the expected pulse peak. The expected pulse transition state has a first falling portion and a second falling portion, and the first and second falling portions cooperate to form a concavely curved falling side; and the controller is to determine with reference to the captured electrical characteristics of the responsive signal whether the response signal is a responsive pulse having a concavely curved falling side, and to send out a control signal indicative of positive living body detection upon a positive outcome of determination.

In some embodiments, the first falling portion is a rapidly falling falling-portion which continues immediately from the expected pulse peak, and the second falling portion is a slower falling falling-portion when ends to join the expected pulse steady state, In some embodiments, the first falling portion falls at a rate resembling a free-fall relative to the second falling portion, and the second falling portion falls following an asymptotic manner.

In some embodiments, the probing pulse rise-time is set to facilitate capture of the expected pulse peak magnitude, and the rise-time is set to correspond to be comparable to a minimum sample-and-hold time requirement of an integrated circuit fast sample-and-hold circuit.

The probing pulse has a preferred period of between 1 ms to 25 ms, so that multiple-pulse detection and analyses can be facilitated in a few seconds or tens of seconds.

The probing pulse preferably has a mark-to-space ratio of between 1-2 to 1-8, including 1-2, 1-3, 1-4, 1-5, 1-6, 1-7, 1-8. A higher mark-to-space ratio facilitates multiple pulse detection and confirmation while allowing sufficient time for a living body to return to its initial unexcited state.

In some embodiments, the probing pulse has a probing pulse rise-time of up to 1.5 µs, including between 300 ns and 1.5 µs.

In some embodiments, the probing pulse has a linear rising edge or a non-linear rising edge, the rising edge having a monotonous rising edge.

In some embodiments, the controller is configured to operate to capture a signal magnitude of the responsive signal at a capture time immediately after the probing pulse has risen from the probing pulse base state to the probing state.

In some embodiments, the controller is configured to operate to capture a plurality of signal magnitudes of the responsive signal during the expected pulse transition state, and a plurality of signal magnitude samples of the responsive signal during the expected pulse steady state.

In some embodiments, the electronic circuit arrangement comprises a pulse broadening circuit to spread the expected pulse peak to a more rounded peak to facilitate measurement of the expected pulse peak magnitude.

The disclosure comprises sending a probing signal to the contact surface, detecting an electrical response signal from the contact surface in response to the electrical probing signal, and determining whether a captured responsive signal has pertinent characteristics of an expected responsive pulse, and to output a positive output signal indicative of possible living body to mitigate risks of electrical shock if some or all pertinent characteristics are detected.

A method of detecting possible living body contact at an electrical contact surface is disclosed. The living body has a detectable characteristic initial impedance and a corresponding characteristic time constant defined by the initial impedance upon touching the electrical contact surface when the electrical contact surface is at a touching voltage.

The method comprises sending a non-hazardous probing signal to the contact surface. The probing signal comprises one probing pulse or a plurality of probing pulses forming a probing pulse train, and the probing pulse has a base voltage level and a probing voltage level which is above the base voltage level and equal to the touching voltage or a probing voltage level which is below the base voltage level and equal to the touching voltage; detecting an electrical response from the contact surface in response to the electrical probing signal. The electrical response comprises electrical response signals; and determining from the electrical response signals whether there is possible living body contact at the electrical contact surface.

The probing pulse rises from the base voltage level to the probing voltage level in a rise time which is substantially shorter than the time constant to define a rising edge and stays in the probing voltage level for a duration substantially longer than the time constant. The probing pulse has a base voltage level and a probing voltage level which is below the base voltage level and equal to the touching voltage. The probing pulse falls from the base voltage level to the probing voltage level in a fall time which is substantially shorter than the time constant to define a falling edge and stays in the probing voltage level for a duration substantially longer than the time constant.

The method comprises comparing the electrical response which is received in response to the probing signal in a time window which defines a detection time period with a reference response and determining whether the electrical response matches with the reference response to decide whether there is living body contact at the electrical contact surface. The reference response is an expected [time domain] response resulting from application of the probing signal to the living body or to a passive electrical impedance network having the characteristic initial impedance of the living body. The reference response is an expected response determined with reference to a plurality of sample responses of a corresponding plurality of living bodies forming a sample pool, and the sample response is obtained by collection of response signals by application of the probing signal to a sample living body of the sample pool individually and each sample living body has a detectable characteristic initial impedance and a corresponding characteristic time constant defined by the initial impedance upon touching the electrical contact surface when the electrical contact surface is at the probing voltage.

The method comprises collecting a plurality of signal magnitude values of the electrical response at a plurality of data collection times, and determining with reference to the plurality of signal values whether the electrical response matches with the reference response to decide whether there is living body contact at the electrical contact surface.

The data collection times are sequentially distributed in a collection time window which begins at a time in close proximity to the rising edge or the falling edge of the probing signal and which has a time duration comparable to or larger than the time constant.

The characteristic initial impedance has a characteristic initial resistance and a characteristic initial capacitance in series, and the time constant defines a time value which is equal to the characteristic initial resistance times the characteristic initial capacitance.

The electrical contact surface has a characteristic contact area and the living body has a characteristic internal resistance and a characteristic skin capacitance determinable with reference to the contact area. The characteristic initial resistance has a resistance value equal to or comparable to the internal resistance and the characteristic initial capacitance has a capacitance value equal to or comparable to the skin capacitance.

The probing pulse has a stepped waveform or a square waveform.

The probing pulse has a voltage level which is sufficient to generate an electronically detectable current inrush into the living body and the current inrush has a non-hazardous peak current magnitude and a non-hazardous duration.

The method comprises a microcontroller operating an electronic circuit to collect the electrical response signals and determining whether the electrical response has time domain characteristics matched or comparable with time domain characteristics of the reference response with reference to the electrical response signals collected.

The method comprises a microcontroller operating an electronic circuit to collect a plurality of signal magnitude values of the electrical response at a plurality of data collection times and determining whether the electrical response has time domain responsive characteristics matched or comparable with time domain characteristics of a passive impedance network having the characteristic initial impedance when subject to an applied step probing signal having a rise time which is negligibly small compared to the time constant.

The method comprises determining whether the electrical response matches with the reference response with reference to one or more time-domain characteristics of the electrical response: peak current magnitude, current spike magnitude, current spike duration, current pulse shape, time constant, current fall time trend or rise time trend, magnitude of steady state current, current zero-crossing presence.

The square pulse has a rise time of less than 5 µs, less than 4 µs, less than 1 µs, less than 2 µs, less than 3 µs, less than 0.5 µs, less than 0.3 µs, less than 0.2 µs, less than or more than 100 ns, more than 50 ns, or a range or any ranges formed by a combination of the aforesaid values.

The square pulse has a probing voltage level duration of between 50 µs and 50 ms, including more than 50 µs, more than or less than 100 µs, more than or less than 200 µs, more than or less than 300 µs, more than or less than 500 µs, more than or less than 1 ms, more than or less than 5 ms, more than or less than 10 ms, more than or less than 20 ms, more than or less than 30 ms, more than or less than 50 ms, or a range or any ranges formed by a combination of the aforesaid values.

The probing voltage level is between 10V and 50V, including at or larger than 10V, at or larger than or smaller than 15V, at or larger than or smaller than 20V, at or larger than or smaller than 25V, at or larger than or smaller than 30V, at or larger than or smaller than 35V, at or larger than or smaller than 40V, at or larger than or smaller than 45V, at or smaller than 50V, or a range or any ranges formed by a combination of the aforesaid values.

The probing signal has a probing signal frequency of between 20 Hz to 2 kHz, including 20 Hz or more, 40 Hz or more or less, 60 Hz or more or less, 80 Hz or more or less, 100 Hz or more or less, 200 Hz or more or less, 400 Hz or more or less, 600 Hz or more or less, 800 Hz or more or less, 1 kHz or more or less, 2 kHz or less, or a range or any ranges formed by a combination of the aforesaid values.

The probing signal is a DC signal.

The responsive signals are current signals.

The time window begins in time proximity to or in alignment with the end of the rising edge or falling edge of the probing signal.

In some embodiments, the method comprises using template matching, pulse shape matching or deep learning to determine whether the electrical response is matched with the reference response.

A load detector for detection of living body contact at a contact surface is disclosed. The living body has a detectable characteristic initial impedance and a corresponding characteristic time constant defined by the initial impedance upon touching the electrical contact surface when the electrical contact surface is at a touching voltage. The apparatus comprises a microcontroller and electronic circuitry and the microcontroller is to operate the electronic circuitry to send a non-hazardous probing signal to the contact surface, detect an electrical response from the contact surface in response to the electrical probing signal, and determine from the electrical response signals whether there is possible living body contact at the electrical contact surface. The probing signal comprises one probing pulse or a plurality of probing pulses forming a probing pulse train, and the probing pulse has a base voltage level and a probing voltage level which is above the base voltage level and equal to the touching voltage or a probing voltage level which is below the base voltage level and equal to the touching voltage. The electrical response comprises electrical response signals.

The probing pulse rises from the base voltage level to the probing voltage level in a rise time which is substantially shorter than the time constant to define a rising edge and stays in the probing voltage level for a duration substantially longer than the time constant. The probing pulse has a base voltage level and a probing voltage level which is below the base voltage level and equal to the touching voltage. The probing pulse falls from the base voltage level to the probing voltage level in a fall time which is substantially shorter than the time constant to define a falling edge and stays in the probing voltage level for a duration substantially longer than the time constant.

A power safety device according to the disclosure comprises a controller, a load detector according to claim 19 comprising electronic circuitry operable by the controller, and power connection circuitry. The power connection circuitry defines a switchable power connection path between a source side and a load side. The power connection circuitry is switchable by the controller to operate in a first operation state or an on-state in which state impedance between the source side and the load side is very low to permit flow of operation current through the power connection circuitry, or a second operation state or an off-state in which state impedance between the source side and the load side is very high to impede flow of operation current through the power connection circuitry. The controller is to operate the load detector according to the method of any preceding claim to determine whether there is possible living body contact at the electrical contact surface and to switch the power connection circuitry to the on-state if outcome of determination is no real likelihood of possible living body contact at the electrical contact surface.

FIGURES

Figure 7A:
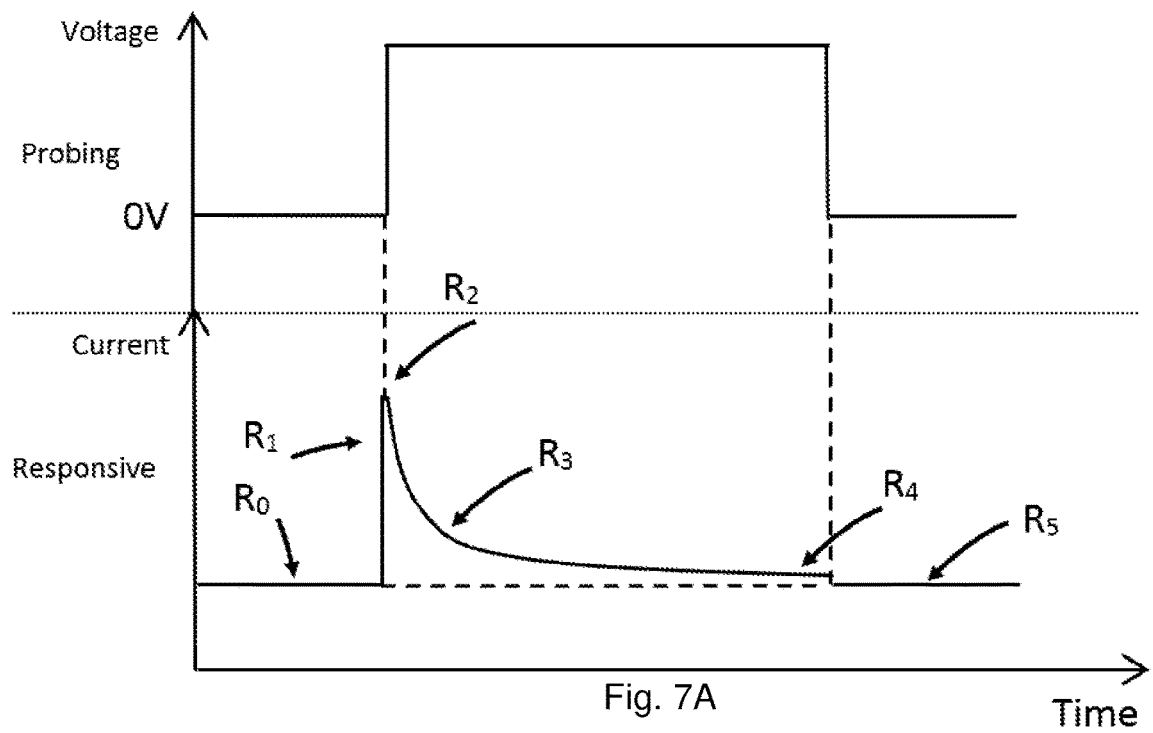
Figure 7B:
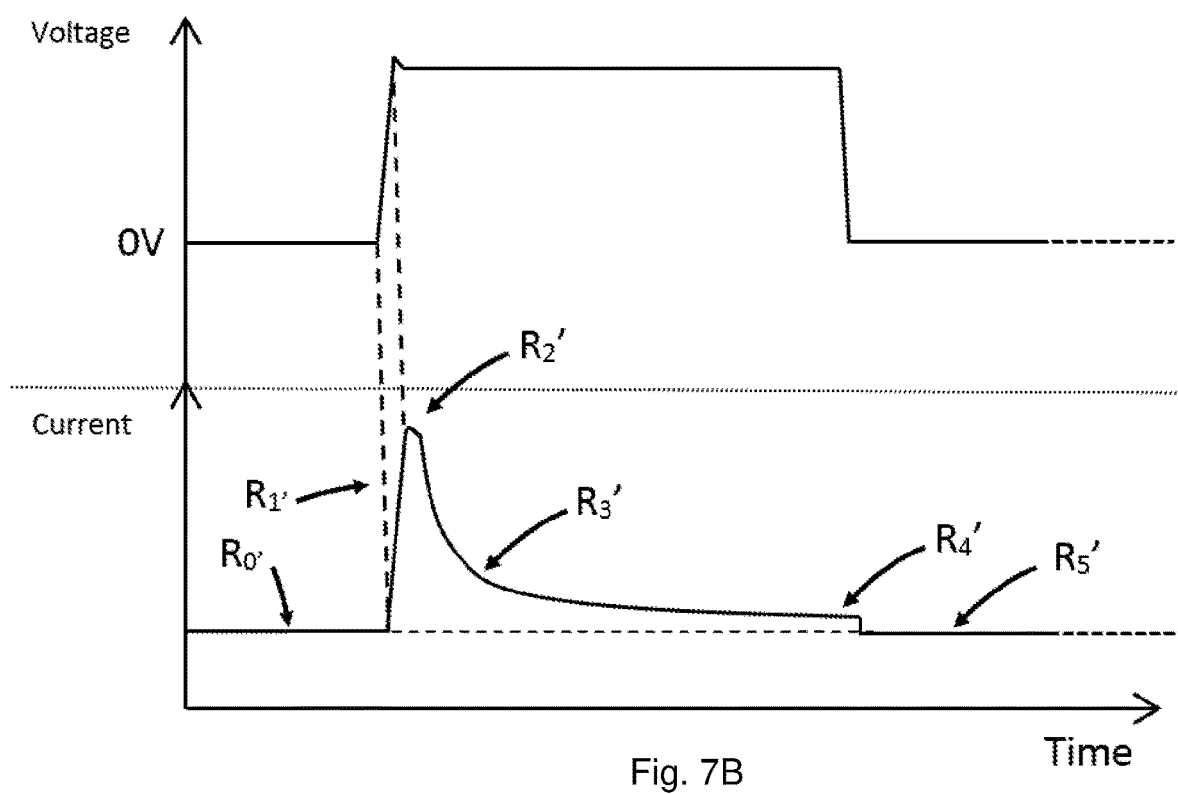
Figure 8A:
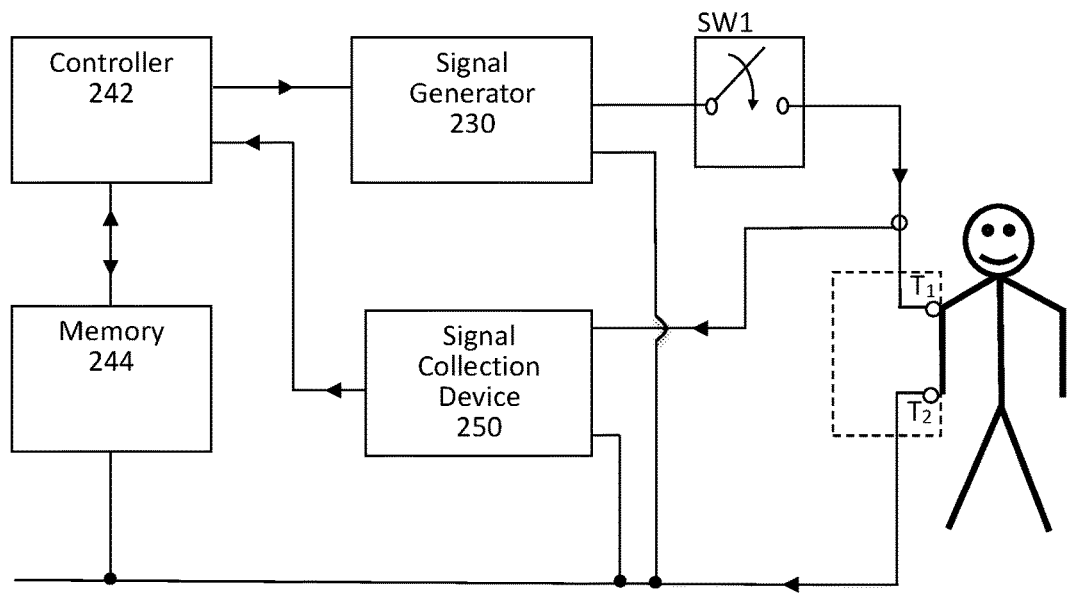
Figure 8B:
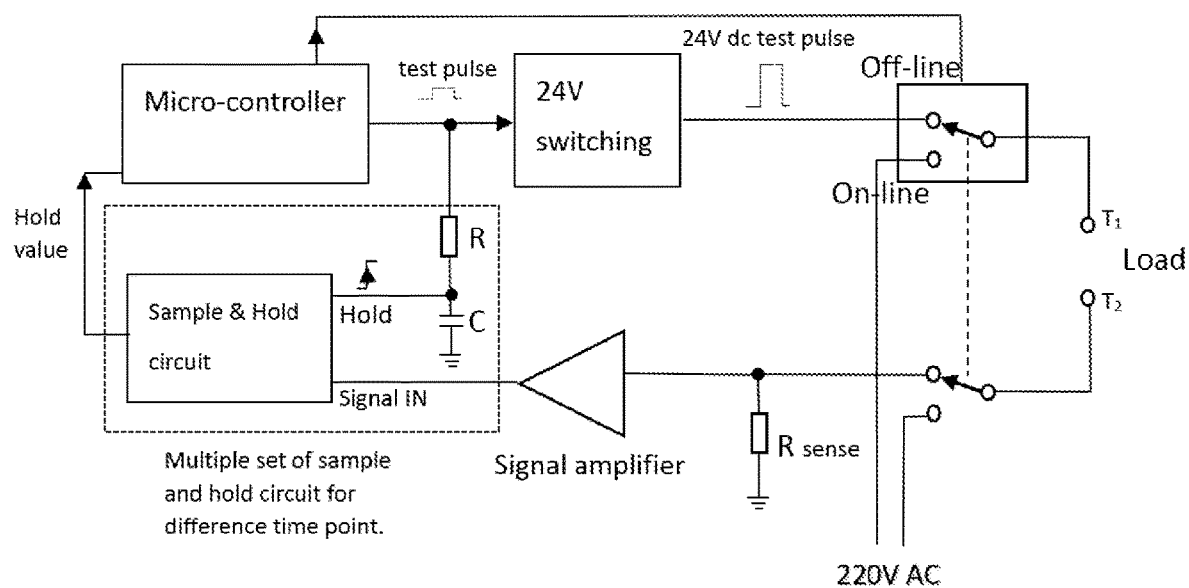
Figure 9A:
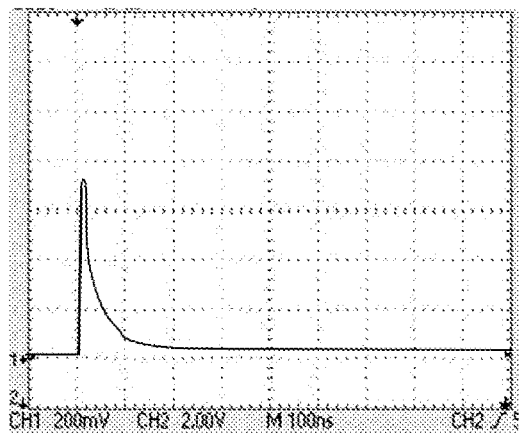
Figure 9B:
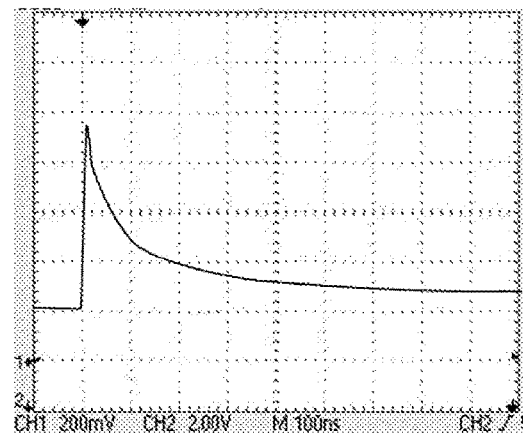
Figure 9C:
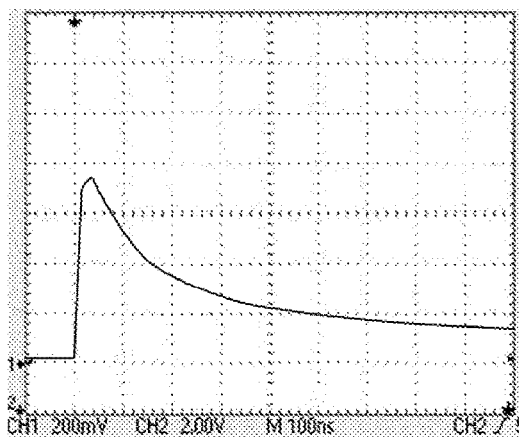
Figure 9D:
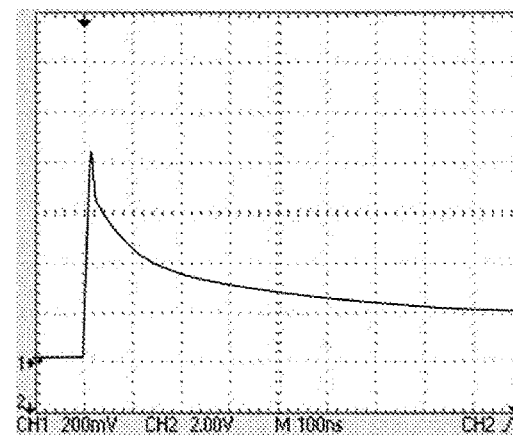
Figure 9E:
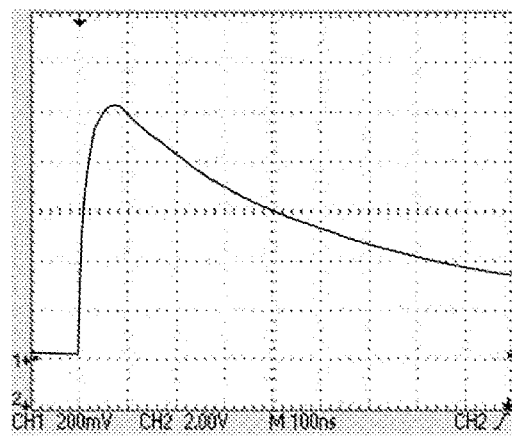
Figure 9F:
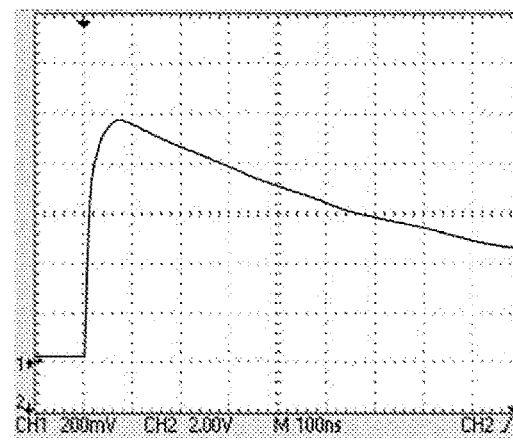

The present disclosure is described by way of example and with reference to the accompanying figures, in which FIG. 1 is a captured image of a sampling oscilloscope displaying an example probing signal applied to a sample living body XCD and an electrical response of XCD, FIGS. 2A1 is a schematic diagram of the measured example probing signal of FIG. 1, FIGS. 2A2 is a schematic diagram of the measured example electrical response of FIG. 1, FIG. 2B1 is a schematic diagram of a simulated probing signal corresponding to the example probing signal of FIG. 1, FIGS. 2B2 is a schematic diagram of a simulated response signal of an electrical response using parameters derived from measurements of FIG. 1, FIG. 2C1 is a schematic diagram of an example probing signal train having positive and negative probing voltages, FIG. 2C2 is a schematic diagram of a simulated response signal to the probing signal train of FIG. 2C1, FIG. 3 is a circuit diagram of an example electronic circuitry of an example detection arrangement for facilitating living body detection on a load side, FIG. 3A1 is a schematic diagram of an example probing signal train for use with the example detection arrangement of FIG. 3, FIG. 3A2 is a schematic diagram showing data collection timing points of the example detection arrangement of FIG. 3, FIGS. 3B1 and 3B2 are flow charts showing example operation flows of the example detection arrangement of FIG. 3, FIGS. 3C1 to 3C7 are schematic diagrams showing example detection criteria to facilitate living body detection using the example detection arrangement of FIG. 3, FIG. 4 is a block diagram of an example detection arrangement for facilitating living body detection on a load side, FIGS. 4A1 and 4A2 are circuit diagrams of a main detection circuit of the example detection arrangement, FIGS. 4B1 and 4B2 are circuit diagrams of parts of the example detection arrangement, FIGS. 4C1 and 4C2 are circuit diagrams of parts of the example detection arrangement, FIG. 5 is block diagram of an example power switching apparatus, FIG. 5A is an example flow chart depicting operation flows of the power switching apparatus of FIG. 5, FIG. 5B is a circuit diagram of an example power switching apparatus of FIG. 5, FIG. 6 is a diagram of a power supply arrangement comprising a power switching apparatus of FIG. 5, FIG. 7A shows, schematically, an example probing pulse and an example expected responsive pulse, FIG. 7B shows, schematically, an example probing pulse and an example expected responsive pulse, plus effect of increasing rise time on pulse peak, FIG. 8A is an example electronic arrangement according to the disclosure, FIG. 8B is another example electronic arrangement according to the disclosure, FIGS. 9A to 9F are example captured responsive pulses of different living bodies or capture conditions, and FIGS. 10A to 10D shows probing signals having different rise times and the corresponding expected responsive pulses.

DESCRIPTION

When a square voltage pulse is applied on a living body portion, a responsive pulse having unique characteristics will appear in response. When a train of square voltage pulses is applied on the living body portion, a train of responsive pulses having unique characteristics will appear in response.

The square pulse has two pulse states, namely, a first state and a second state. The first state is a base state having a base voltage. The second state is an elevated state having an elevated voltage. Each square pulse is at the first state and at the base voltage when at time zero, and rises to reach the second state in a time known as the rise-time of the square pulse. The rise from the base state to the elevated state defines a rising edge of the square pulse. The square pulse then stays at the second state and at the elevated voltage level for a duration to define a 'mark' portion having a mark duration. The square pulse returns to the base state at the end of the elevated duration and stays at the base state until the end of the pulse period. The time of stay at the base state defines a 'space' portion having a space duration. The fall from the elevated state to the base state defines a falling edge of the square pulse. Adjacent rising edges to adjacent square pulses define the pulse period of the square pulse.

Each responsive pulse is a current pulse comprising a rising side, a falling side, and a pulse peak dividing the rising side and the falling side, as depicted in FIG. 7A. Adjacent responsive pulses are separated by a separation time which is equal to the separation time between corresponding adjacent square pulses.

The responsive pulse has an initial state $R_0$, a rising state $R_1$, a peak state $R_2$, $R_2'$, a falling state $R_3$, $R_3'$, a steady state $R_4$, $R_4'$ and a final state $R_5$, $R_5'$.

The responsive pulse rises from a base level at the initial state and reaches the pulse peak of the peak state in a rise time. The responsive pulse falls from the pulse peak to a steady-state level of the steady state and stays at the steady state and the steady state level until the end of the steady state. The responsive pulse then falls from the steady state level to the base state level and stays at the base state level until the end of the response pulse period. The initial state and the base level are at the same electrical level. The falling side comprising a first falling portion and a second falling portion. The first falling portion falls more rapidly than the second falling portion. The first falling portion begins immediately at the response pulse peak and falls at a rapid rate to define a pulse spike in cooperation with the rising side. The second falling portion falls slowly to reach the steady-state level in a fall time and stays at the steady state level until the end of the responsive pulse period. The first falling portion and the second falling portion cooperate to define a concavely curved falling side.

The rising side of the responsive pulse closely follows the rising edge of the square pulse. The falling side of the responsive pulse is independent of the rising edge but is dependent on the responsive pulse peak and occurs immediately after the responsive pulse peak.

The example square pulse of FIG. 7A has a very short pulse rising time, for example, of less than 50 ns, and a pulse cycle of 21 ms, and a mark and space duration ratio of 1:3. The mark duration is approximately 5 ms and the space duration is selected to be substantially longer than the mark duration to permit a living body to relax or to electrically reset from excitation by a probing pulse. The base voltage is 0V while the elevated voltage is 24V in this example.

When the rise time of a square pulse increases, the rise time of the responsive pulse also increases, but is still in line with the rising time of the square pulse, although the responsive pulse peak begins to show roundness such that the responsive pulse peak is a rounded peak, instead of a spiky peak.

It is noted that when the rising time of the square pulse increases further, that is, the square pulse is slower rising, the responsive pulse peak will become more rounded and the magnitude decreases, compared to the fast rising-time peak magnitude.

A living body responds with a responsive pulse having unique electrical pulse characteristics when subject to direct application of square pulses. It is an aspect of the present disclosure to utilize square pulses as a probing signal to perform detection of living body contact.

When a living body touches a live electricity source, for example, the AC mains, the initial electrical responses of the exposed portion of the living body which is in physical and electrical connection with the electricity source can be estimated or predicted using an accepted equivalent circuit of a living human body. The equivalent circuit is an impedance network comprising a first impedance portion, a second impedance portion and a third impedance portion which are connected in series to form an impedance bridge.

The first impedance portion comprises a first resistor of a first resistance value R_1 and a first capacitor in parallel connection with the first resistor to form a first R-C bridge and having a first capacitance value C_1. The second impedance portion comprises a second resistor of a second resistance value R_2 and a second capacitor in parallel connection with the second resistor and having a second capacitance value C_2. The third impedance portion comprises a third resistor of a third resistance value R_3 and a third capacitor in parallel connection with the third resistor and having a third capacitance value C_3. The first impedance portion is believed to represent a first skin impedance Z_p1. The second impedance portion is believed to represent a body internal impedance Z_i. The third impedance portion is believed to represent a second skin impedance Z_p2.

The impedance value of the impedance network in frequency domain or Laplace domain is set out in equation (1) below.

$$Z(s) = \left(R_1 // \frac{1}{sC_1}\right) + \left(R_2 // \frac{1}{sC_2}\right) + \left(R_1 // \frac{1}{sC_1}\right) = \frac{R_1}{1+sR_1C_1} + \frac{R_2}{1+sR_2C_2} + \frac{R_1}{1+sR_1C_1} \quad (1)$$

The frequency domain response of equation (1) is based on the assumptions that the first and the second impedance values are identical and there is no initial stored energy in the capacitors. These assumptions should hold for studies of non-hazardous transient electrical shock on a living body where the contact time and area are small.

When a voltage V(s) is applied to the impedance network, the responsive current is given by the relationship described in equation (2) below.

$$I(s) = \frac{V(s)}{Z(s)} = \frac{\frac{k}{s-a} - \frac{k}{s}}{\frac{2R_1}{1+sR_1C_1} + \frac{R_2}{1+sR_2C_2}} \quad (k < 0, \ a < 0) \quad (2)$$

When a voltage step pulse is applied across the terminals of the impedance network on the impedance network as a probing signal, the time domain current response i(t) of the impedance network can be represented by the expression of equation (3) below.

$$i(t) = L^{-1}[I(s)] = -\frac{k}{2R_1 + R_2} + \quad (3)$$

$$ke^{at}\frac{(1+aR_1C_1)(1+aR_2C_2)}{2R_1R_2 + aR_1R_2C_1 + 2aR_1R_2C_2} - 2ake^{-t\left(\frac{2R_1+R_2}{R_1R_2(C_1+2C_2)}\right)}$$

$$\frac{(R_1C_1 - R_2C_2)^2}{(C_1+2C_2)(2R_1+R_2)(2R_1+R_2+aR_1R_2C_1+2aR_1R_2C_2)}$$

A voltage step in the frequency domain is represented by equation (4) below and has a time domain representation of equation (5) below.

$$V(s) = \frac{k}{s-a} - \frac{k}{s} \quad (k < 0, \ a < 0) \quad (4)$$

$$V(t) = ke^{at} - k \quad (k < 0, \ a < 0) \quad (5)$$

The steady state current i(t)_ss of the responsive pulse can be obtained by equation (6) below.

$$i(t)_{ss} = \lim_{t \to \infty} i(t) = -\frac{k}{2R_1 + R_2} \quad (k < 0) \quad (6)$$

The magnitude of the steady-state current is equal to $$\frac{v}{2R_1 + R_2}$$

and the magnitude of the in-rush current or current peak is equal to $$\frac{v}{R_2}.$$

The rise time, or the time from the zero current to peak current, of the responsive pulse can be determined using equation (3) by setting $$\frac{di(t)}{dt} = 0,$$

and this will give equation (7) below.

Equation 7:

$$t_{rise} = \frac{1}{a + \left(\frac{2R_1 + R_2}{R_1R_2(C_1 + 2C_2)}\right)} \ln - \\ 2\frac{(R_1C_1 - R_2C_2)^2}{\frac{(C_1+2C_2)^2(2R_1+R_2+aR_1R_2C_1+2aR_1R_2C_2)}{(1+aR_1C_1)(1+aR_2C_2)}}{2+aC_1+2aC_2}$$

The response current pulse comprising a peak current, a rising side current on one side of the peak current and a falling side on another side of the peak current. The rising side current is characterised by equation (3), when the time is less than $t_{rise}$, the falling side current is characterised by equation (3), when the time is larger than $t_{rise}$, and the current peak occurs at time=$t_{rise}$ and having a responsive pulse peak magnitude.

The time domain current response i(t) of the impedance network when subject to a step voltage pulse, as represented by equation (2), is a current pulse having unique characteristics which are representative of living body and step voltage pulses are to be used as probing signals for living body detection herein.

For the present purposes, the internal capacitance $C_2$ is substantially smaller than the skin capacitance $C_1$ and can be ignored to further simplify the equations.

It is apparent from equation (7) that the rise time of the responsive current is dependent on the network impedance.

To facilitate detection of possible electrical contact of a living body, especially a living human body or body portion, with a live contact surface, schemes, methods, apparatus and devices are disclosed herein. In light of the uniqueness of the responsive current pulses that can be expected when a living body is subject to excitation by a square-pulse based voltage signals, square-pulse based voltage signals are disclosed herein for use as probing signals.

A probing signal herein may comprise one square pulse, although the probing signal may be a train of pulses formed by a plurality of identical square voltage pulses. The identical probing pulses may be used for confirmation of initial outcome of determination or for other purposes, for example, determination of whether the responsive signal contains parameters indicating dynamic behaviour of a living body. The square pulses forming a signal train may not be identical. Non-identical probing pulses may be used by a micro-controller to determine when the subject giving a responsive signal contains non-linear electrical parameters of a living body.

To facilitate non-harmful detection, the probing signals disclosed herein have electrical characteristics, including current and voltage magnitudes, pulse durations, pulse repetition frequencies, which are non-harmful to a living body. Non-harmful herein includes non-hazardous.

To mitigate discomfort or concern of a living body subject which is in contact with a contact surface adapted for detection of living body contact, and to mitigate the risks of panicking, the responsive signal is controlled to below a threshold current peak. The threshold current peak is selected to be at around 10 mA to 20 mA, a higher peak current threshold may be used, but with caution.

A probing signal of the present disclosure is a voltage signal comprising a probing voltage pulse as a probing pulse. The probing pulse is a square pulse described herein and has a first state and a second state. The first state in this disclosure is at a base state voltage of 0V. The second state is at an elevated voltage above the base state voltage.

A probing pulse herein preferably has a very short rise time with respect to the impedance network, so that the skin capacitors $C_1$ would behave electrically as a short-circuit during the probing pulse rise time. On the other hand, the probing pulse rise time should not be so short to make the internal capacitance $C_2$ also behave electrically as a short-circuit during the probing pulse rise time. Since the internal capacitance $C_2$ has a significant smaller capacitance value than the skin capacitor $C_1$, for example, $C_2$ has a capacitance value of less than 1%, 5% or 10% of the capacitance value of the skin capacitor $C_1$, a fast rise time of between 20 ns and 50 ns would strike a good balance of making the skin capacitor $C_1$ a short circuit while making the internal capacitance $C_2$ behave electrically as an open circuit during the probing pulse rise time. Where the probing pulse is such that the skin capacitors $C_1$ behave as a short circuit and the internal capacitance $C_2$ behaves as an open circuit during the probing pulse rise time, the responsive pulse will reach a current peak at the end of the probing pulse rise time, and the responsive pulse peak will have a responsive pulse peak current having a value of $$\frac{v}{R_2},$$

where is the elevated state voltage, that is probing voltage.

Since the probing pulse is to stay at the probing state voltage after having risen from the base state voltage and reached the probing state voltage, and will stay at the probing state voltage during the entire probing state duration, the non-change of voltage at the entire probing state means that the charged skin capacitors $C_1$ will begin to discharge immediately after reach the current peak and the discharge will result in a current following the time-domain characteristics of equation (3).

An example electronic circuit arrangement for detection of possible living body contact comprises a micro-controller 242, a signal generator 230, a data storage device 244, a signal collection device, a switch SW1 and a pair of contact terminals T1, T2, as depicted in FIG. 8A.

The controller 242 is to operate the signal generator 230 to generate a probing pulse to the probing terminals T1, T2, which are disposed on a contact surface which a living body may come into physical and electrical contact. The signal collection device is to collect response signals from the contact terminal T1. The controller 242 is to store responsive signals collected from the contact terminal T1 in the data storage device 244 and to perform analyses to determine whether a detected responsive signal has the characteristics representative of a living body. If the outcome of determination is that the detected responsive signal has the characteristics representative of a living body, the controller 242 will generate a control signal indicative of likely hazardous conditions. The controller may be a micro-controller or a micro-processor based solid state controller. The controller may determine whether the responsive pulse carries the characteristics representative of a living body with respect to the parameters of the captured responsive pulse, including the peak current magnitude, the steady state current magnitude, whether there is zero crossing of the responsive pulse, the fall-time characteristics of the responsive pulse fall side, or any combination of any of the aforesaid collected electrical parameters.

While an abrupt step voltage pulse having a fast rise time would produce a responsive pulse peak having a peak current magnitude of $$\frac{v}{R_2},$$

the peak may be too sharp to capture.

To alleviate the problem, a pulse broadening device may be connected at the output of the signal collection device 250, as depicted in FIG. 8B. The example pulse broadening device is an operational amplifier Op-amp MAX4012 which operates to broaden a sharp pulse to one having a width of about 300 ns.

In other embodiments, the probing pulse is shaped such that the rise time is increased to result in a responsive pulse having a rounded peak, as depicted in FIG. 7B. For example, the rise time may be increased to between 200 ns to 1.5 us, so that a response having a rounded magnitude with approximately the same magnitude of an expected responsive pulse can be obtained. The rise time may be for example, 200 ns, 300 ns, 400 ns, 500 ns, 600 ns, 700 ns, 800 ns, 900 ns, 1 us, 1.1 us, 1.2 us 1.3 us, 1.4 us, 1.5 us, 1.6 us, or any range or ranges obtained from a combination of the aforesaid values. The rise edge may be a linear rising edge or a non-linear rising edge, such as one having rising RC-characteristics.

Example expected responsive pulses having rise times of 1 us, 5 us, 10 us, 15 us of an example living body target are shown respectively in FIGS. 10A to 10B.

It will be appreciated that even though the electrical parameters of living bodies vary to a large degree and the variation can change according to capture conditions, the responsive pulses of a living body when subject to probing pulses herein follow a similar pattern, as depicted in FIGS.

7A, 7B, and 9A to 9F. Therefore, the use of the probing signal and the comparison between captured responsive signal and the expected response pulse can serve as operable guidelines for determination of possible living body contact at the contact surface or the contact terminals. As a reference, the peak currents of the living body of FIGS. 9A to 9F are respectively, 2.5 mA, 6.3 mA, 12.6 ma, 2.7 mA, 8.15 mA and 15.9 mA.

While the disclosure has been described herein with reference to examples, the examples are to assist understanding and are not intended and should not be used to limit the scope of disclosure. For example, while Lithium ion batteries have been used as examples herein, the arrangement and devices herein apply to other types of batteries without loss of generality.

FIG. 1 shows an example probing signal (upper channel) which is applied to a living body and the current response or responsive current (lower channel) captured by a sampling oscilloscope in an example measurement. The example probing signal is in the form of a pulsing train consisting of a plurality of probing pulses and the probing pulses are separated at regular intervals. The example probing signal has a frequency of 1 kHz at 50% duty ratio and a nominal voltage of 10V and each example probing pulse is a square pulse having a base voltage and a touching voltage above the base voltage. The example touching voltage is at 20V. The example probing signal is applied to a living body object with a contact area of 100 mm$^2$ and a 500 g force contact pressure.

The current response to the applied probing signal shown in FIG. 1 has a responsive pattern which is the same as the aforesaid regular pattern of current responses obtained when a living body touches a contact surface at an elevated touching voltage.

Referring to FIG. 1, the response current rises very rapidly from zero to reach a current peak having a peak current amplitude $I_{max}$ within a very short rise time and then falls off monotonously to an asymptotic steady state and minimum current value $I_{steady\_state}$. The rise of the responsive current from zero current to peak current is almost instantaneous or is almost synchronized with the rising of the probing signal. The current peak occurs at almost the same time as the time when the probing pulse reaches the touch voltage level. The magnitude of the responsive current falls very rapidly or sharply initially after reaching the current peak and then falls slowly to reach a steady state current. The fall is monotonous, that is, not oscillatory, and the falling portion has a concave shape. The rapid rise represents a current inrush and the rapid initial rise and the rapid initial fall of the responsive current cooperate to form a current pulse. % The rapid initial rise, the rapid initial fall and the subsequent slow fall continued from and after the initial rapid fall of the responsive current cooperate to form a non-symmetrical current pulse.

Measurements revealed that the peak current amplitude $I_{max}$ appears to relate to the amplitude of the touch voltage, $V_{touch}$, by the approximate relationship of $V_{touch}=I_{max}R_0$ and the falling portion of the responsive current, comprising both the initial rapid fall portion and the subsequent slow fall portion, appears to resemble the falling or discharge characteristics of a serially connected RC circuit.

Further measurements of additional living body samples revealed that the peak current amplitude $I_{max}$ relates to the amplitude of the touch voltage, $V_{touch}$, by the approximate relationship of $V_{touch}=I_{max}R_0$, and the responsive current falling characteristics do resemble the falling or discharge characteristics of a serially connected RC network having a resistive value $R_0$ and a capacitive value $C_0$ connected in series and the current falling characteristics can be represented by the relationship: $i(t)=I_{max}e^{-t/\tau}$, where i(t) is the magnitude of the responsive current at time t from the current peak and $\tau$ is a time constant equal to $R_0 \times C_0$. For the example living body, XCD, the circuit parameters are estimated from the measured current peak magnitude $I_{max}=6.65$ mA and the falling characteristics and are found to be approximately: $R_0=1.5(4)k\Omega$ and $C_0=5.46$ nF.

Simulated responses using the above parameters and applied probing conditions are shown in FIGS. 2A1 and 2A2. The measured time responses are shown in FIGS. 2B1 and 2B2. Simulation time responses using the parameters and probing conditions of FIGS. 2A1 and 2A2 and showing more pulses are shown in FIGS. 2C1 and 2C2. The simulated results and experimental results appear to agree well. The example probing pulse train of FIG. 2C1 is in fact an AC pulse train comprising both positive and negative probing voltage levels. As a result, the electrical response comprises both positive current pulses and negative current pulses. The positive current pulse has a sharp rising edge to reach a positive current peak followed by a falling curve. The negative pulse comprises a sharp falling edge to reach a current trough or a negative peak current followed by a rising current curve. In the present disclosure, the term "rising to a current peak" also means rising in a negative direction to the negative current peak and the term falling current would mean a rising current curve of a negative current pulse and the related description is to apply mutatis mutandis wherein appropriate for succinctness without loss of generality.

Experimental and simulation results of additional sample living bodies show that a living body appears to behave electrically like a serially connected RC network having a resistance value $R_0$ and a capacitance value $C_0$ connected in series when subject to an applied stepped probing voltage. The resistance $R_0$ and the capacitance $C_0$ are respectively referred to as initial resistance and initial capacitance herein.

It is noted that the value of the initial resistance $R_0$ is approximately equal to the value of the internal resistance $R_i$ of the human body and the value of the initial capacitance $C_0$ is close to the value of the skin capacitances $C_{p1}$ and $C_{p2}$ in series.

It is noted that the linear relationship between the amplitude of the touch voltage and the amplitude of the peak current, that is, $V_{touch} \approx I_{max}R_0$, holds when the rise time of the step voltage pulse is short enough so that the skin capacitances $C_{p1}$ and $C_{p2}$ has a very low impedance to bypass the resistive effect of the skin resistances, but the rise time should be not too short to make the impedance of the internal capacitive element $C_i$ which is in parallel with the internal resistance $R_i$ too low to provide a significant or noticeable bypass current path to the internal resistance $R_i$.

When the rise time of the applied step voltage is short enough to have the skin resistors $R_{pi}$ bypassed or substantially bypassed by the negligibly low impedance of the skin capacitor $C_{pi}$ but not too short to cause bypass of the internal resistance $R_i$ by the internal capacitance $C_i$, the initial impedance of the human body at the instant of touching is primarily the initial resistance $R_0$ which is substantially equal to the internal resistance $R_i$ of the human body. When under the aforesaid conditions, the skin impedance $Z_{p1}$ and $Z_{p2}$ becomes very low and negligible so that the skin resistance is substantially bypassed, and the impedance value of the internal impedance is primarily or substantially that of the internal resistance $R_i$ since the impedance of the internal capacitance $C_i$ is still very high when compared to the impedance value of the internal resistance $R_i$ as the rise time is not short enough so that there is no noticeable or significant bypass of the internal resistor $R_i$ by the internal capacitance $C_i$. Studies show that the total body impedance of a living body when subject to an applied probing voltage of 10V sinusoidal AC approaches an asymptotic value approximately at around 10 kHz to 20 kHz, the skin capacitances $C_{pi}$ would appear to have a 3 dB cutoff frequency $f_H$ at around 10 kHz to 20 kHz (source: British standard document PD6519-1:1995, FIG. 6). Therefore, a stepped probing signal having a 10%-90% rise time $t_r$ below 17.5 µs according to the relationship: $f_H \approx 0.35/t_r$ should meet the requirements. In the experiments, the applied probing signals has a rise time from a zero voltage or a base voltage to the touch voltage level of between 100 ns and 200 ns. In general, a zero to touch voltage level rise time at or below 10 µs or 5 µs would be good enough. On the other hand, as the internal capacitance $C_i$ in the magnitude of several pF, a rise time larger than several nanoseconds (ns) should be sufficient to meet the requirements.

Example measured initial resistance $R_0$ and initial capacitance $C_0$ of the sample living body XCD with 100 mm² and 10 mm² contact area at 10V square pulse probing signal and various probing frequencies are set our below:

electrical contact surface before electrical power is supplied to the contact surface or during supply of electrical power to the contact surface. A contact surface herein means an electrical contact surface or a conductive contact surface unless the context requires otherwise.

Experiments on a plurality of sample living human bodies forming a pool revealed that living human bodies have example electrical responsive characteristics in the following ranges:

| 10 V | | | |
|---|---|---|---|
| (20 V Peak-Peak) | R(kΩ) | 2.60 (max) | 0.88 (min) |
| 18 V | $I_{max}$ (mA) | 7.7 (min) | 22.6 (max) |
| (36 V peak-peak) | R(kΩ) | 5.33 (max) | 2.18 (min) |
| 25 V | $I_{max}$ (mA) | 6.76 (min) | 16.5 (max) |
| (50 V peak-peak) | R(kΩ) | 13.05 (max) | 5.49 (min) |
| | $I_{max}$ (mA) | 3.83 (min) | 9.1 (max) |

TABLE 1

(100 mm² contact area)

| | Frequency | 50 | 100 | 200 | 500 | 1k | 2k | 5k | 10k | 20k |
|---|---|---|---|---|---|---|---|---|---|---|
| 10 V | R | 1.50 | 1.52 | 1.52 | 1.52 | 1.50 | 1.54 | 1.52 | 1.54 | 1.64 |
| | C | 5.82 | 5.92 | 5.98 | 5.92 | 5.94 | 5.68 | 5.75 | 5.62 | 5.01 |
| | 2.3xRC | 20.13 | 20.73 | 20.93 | 20.73 | 20.53 | 20.13 | 20.14 | 19.93 | 18.90 |
| | $I_{max}$ (mA) | 6.65 | 6.57 | 6.57 | 6.57 | 6.65 | 6.49 | 6.57 | 6.49 | 6.10 |
| 18 V | R | 1.61 | 1.64 | 1.61 | 1.61 | 1.61 | 1.61 | 1.61 | 1.61 | 1.70 |
| | C | 5.01 | 5.024 | 5.12 | 5.06 | 5.01 | 5.01 | 4.74 | 4.58 | 4.15 |
| | 2.3xRC | 18.51 | 18.91 | 18.91 | 18.71 | 18.52 | 18.51 | 17.52 | 16.92 | 16.23 |
| | $I_{max}$ (mA) | 11.2 | 11 | 11.2 | 11.2 | 11.2 | 11.2 | 11.2 | 11.2 | 10.59 |
| 25 V | R | 1.51 | 1.52 | 1.44 | 1.43 | 1.43 | 1.44 | 1.54 | 1.58 | 1.67 |
| | C | 6.09 | 6.59 | 7.23 | 6.48 | 6.67 | 6.32 | 6.28 | 5.85 | 5.19 |
| | 2.3xRC | 21.1 | 23.12 | 23.90 | 21.30 | 21.91 | 20.9 | 22.30 | 21.3 | 8.67 |
| | $I_{max}$ (mA) | 16.6 | 16.4 | 17.4 | 17.5 | 17.5 | 17.4 | 16.2 | 15.8 | 14.97 |

TABLE 2

(10 mm² contact area)

| | Frequency | 50 | 100 | 200 | 500 | 1k | 2k | 5k | 10k | 20k |
|---|---|---|---|---|---|---|---|---|---|---|
| 10 V | R | 2.02 | 2.083 | 2.19 | 2.02 | 2.08 | 2.02 | 2.05 | 2.08 | 1.95 |
| | C | 1.04 | 1.00 | 0.95 | 1.00 | 0.95 | 1.00 | 0.97 | 0.93 | 1.12 |
| | 2.3xRC | 4.84 | 4.74 | 4.64 | 4.64 | 4.56 | 4.66 | 4.55 | 4.46 | 5.02 |
| | $I_{max}$ (mA) | 4.96 | 4.8 | 4.72 | 4.96 | 4.8 | 4.96 | 4.96 | 4.88 | 4.8 |
| 18 V | R | 1.97 | 2.10 | 2.20 | 2.12 | 2.18 | 2.14 | 2.20 | 2.11 | 2.16 |
| | C | 1.37 | 1.25 | 1.25 | 1.30 | 1.21 | 1.20 | 1.19 | 1.22 | 1.19 |
| | 2.3xRC | 6.21 | 6.04 | 6.32 | 6.33 | 6.05 | 5.92 | 6.02 | 5.97 | 2.57 |
| | $I_{max}$ (mA) | 9.14 | 8.58 | 8.18 | 8.5 | 8.26 | 8.41 | 8.42 | 8.18 | 8.5 |
| 25 V | R | 2.08 | 2.05 | 2.12 | 2.12 | 2.16 | 2.16 | 2.05 | 2.05 | 2.19 |
| | C | 1.24 | 1.21 | 1.16 | 1.11 | 0.93 | 0.99 | 1.24 | 1.25 | 1.17 |
| | 2.3xRC | 5.92 | 5.72 | 5.63 | 5.42 | 4.62 | 4.92 | 5.84 | 5.90 | 5.89 |
| | $I_{max}$ (mA) | 12 | 12.2 | 11.8 | 11.8 | 11.6 | 11.6 | 11.6 | 12.2 | 12.2 |

The magnitude of the inrush current which flows into the human body in response to the stepped voltage touching falls after reaching the current peak. The in-rush current falls very rapidly, sharply or steeply initially and then falls at a substantially reduced falling rate to reach an asymptotic or steady state current value. The steady state current is believed to relate to the amplitude of the touch voltage, $V_{touch}$, by the approximate relationship of $V_{touch} = I_{steady\_state} R_T$, where $R_T$ is a sum of the resistors connected in series and equals $R_{p1} + R_i + R_{p2}$.

The falling of the inrush current follows the discharge characteristics of a series RC circuit.

To promote safe use of electrical power and to mitigate risks of electrical shocks, there is disclosed a method of determining whether there is living body contact at an The above maximum and minimum values define limits of ranges of internal resistance and can be used as range of parameters of electrical responsive characteristics of a living body for characterization of human contact according to the present disclosure.

Studies and experiments suggest that the typical electrical response patterns of a living body when subject to a probing signal having a stepped or square probing pulse is characteristic or representative of a living body and is utilized herein to determine whether there is living body contact at a contact surface.

It transpired from studies and experiments that it is possible to determine whether there is living body contact at a contact surface with reference to one or more time-domain characteristics of the response signals of a living body when subject to a stepped probing signal:

The response signal is in the form of a current pulse.

The responsive current pulse has a single current peak.

The responsive current pulse has a single current spike which is salient and dominant.

The single current spike has a spike magnitude which is substantial compared to the peak current magnitude (for example, has a magnitude of more than 15% or more, 20% or more or less, 25% or more or less, 30% or more or less, 35% or more or less, 40% or more or less of the peak current magnitude, or a range or any ranges formed by combination of the aforesaid values.)

The responsive current follows the probing signal almost instantly to form a current spike and the current spike is followed by a flaring responsive current portion which changes more slowly to reach steady a state current.

The responsive current pulse is non-symmetrical in the time domain.

The non-symmetrical current pulse rises sharply or rapidly to the current peak, falls rapidly from the current peak for an initial period, and then falls slowly in a subsequent period after the initial period of rapid fall to reach a steady state current.

The responsive current pulse has a peak current magnitude (representative of the value of the initial resistance or internal resistance) which is within a range corresponding to a typical range of living body internal resistance.

The responsive current pulse falls from the current peak and the fall follows the fall characteristics of a discharging serial RC network.

The responsive current pulse has a fall time within a predictable range or a typical range.

The responsive current pulse is to arrive at a non-zero steady state current after the subsequent period of falling.

The responsive current pulse is non-zero crossing.

The responsive current falls monotonous and non-oscillatory to reach the non-zero steady state current.

The responsive current rises monotonous and non-oscillatory to reach the current peak.

The responsive current has a fall time (for example a fall of 90% from the peak to the steady state current) which is within a predictable range or a typical range.

The steady state current is less than 10% of the peak current magnitude.

The responsive current has a fall time which is substantially longer than the rise time, that is, the responsive current has a rise time which is substantially shorter than the fall time. For example, the fall time is more than 10 times, 20 times, 30 times or more of the rise time.

The probing signal may comprise a single probing pulse or a plurality of probing pulses forming a probing pulse train. Where the probing signal comprises a plurality of probing pulses, the responses to the plurality of probing pulses may be compared to facilitate determination using more than one results.

The probing signal is a non-hazardous signal having a non-hazardous amplitude and a non-hazardous signal duration.

For example, the probing pulse is a stepped pulse or a square pulse having a non-hazardous probing signal magnitude of less than 50V. An example probing signal has a probing voltage magnitude of 10V or above to ensure a wider dynamic range of detection.

The response characteristics may be selected and used in combination to form a set of decision criteria to facilitate determination of whether there is living body contact at a contact surface.

An example detection arrangement to facilitate determination of whether there is living body contact at a contact surface is depicted in FIG. 3. The detection arrangement comprises a test port which is connected to a +24V voltage source via a high-speed switch Q2. The test port comprises two pieces of metal contact which are separated by 5 mm and each of which has a dimension of 5 mm×1.5 mm and an area of 7.5 mm$^2$. The two metal contacts cooperate to form a bare conductive contact surface. When a voltage is applied to the metal contact which is directly connected to the switch Q2, the contact surface becomes a contact surface at an elevated voltage. The high-speed switch Q2 (IRFL9014) is an N channel MOSFET. One of the test port is connected to the MOSFET switch and the other test port is connected to a current sensing resistor. The current resistor has a first terminal which is connected to the test port and a second terminal which is grounded. The example current resistor is a 25-ohm resistor. The first terminal of the current sensing resistor is connected to an operational amplifier Max4012 and the output of the operational amplifier is connector to an array of sample-and-hold devices AD783. Output of the sample-and-hold devices are connected to input ports of a microprocessor.

The array of sample-and-hold devices are arranged to capture signal levels at the current sensing end of the current sensing resistor at different times (Points 1 to 6). In this example, the various signal collection times are set by the RC networks of the array of 74HC14 hex inverting Schmitt trigger and the parameters are set out below.

| | Point 1 | Point 2 | Point 3 | Point 4 | Point 5 |
|---|---|---|---|---|---|
| R | R1 = 7.5K | R2 = 43.5K | R3 = 62K | R4 = 187K | R5 = 387K |
| C | C1 = 30 pf | C230 pf | C3 = 60 pf | C4 = 100 pf | C5 = 100 pf |
| Delay Time | Current peak | 1.2 μs | 3 μs | 15 μs | 30 μs |

During operation, the microprocessor, operating at 16 MHz, generates a detection signal to the input terminal μP D1 of the detection arrangement. The detection signal is in the form of a detection pulse train and each detection pulse is a stepped or square probing pulse having electrical properties suitable for detection of possible living body contact as described herein. The example probing pulse has a signaling period of 16 ms, a touch voltage level (or elevated voltage level) of 24V for a duration of 1.5 ms, a rise time from zero to the touch voltage of about 100 ns-200 ns and a zero voltage or base level duration of 1 ms, as depicted in FIG. 4A.

When a living body closes the test ports by his/her body part, for example, a finger, the probing pulse will be transmitted to the body part via the MOSFET switch and the current response of the living body to the detection signal will be transmitted to the microprocessor by the sample-and-hold devices.

The signal collection times of the detection arrangement are distributed at several salient regions to facilitate collection of responsive current data at different times, as depicted in FIG. 3A2. For example, point 1 is empirically set at the current peak time, point 2 to is set at the initial rapid falling region, point 3 to is set at the subsequent slow falling region, point 5 is set at the steady state current region, and point 4 is set at a time intermediate points 3 and 5, for example, approximately mid-way between points 3 and 5.

The example detection arrangement has a maximum output voltage of 3.83V and is operable in a high gain mode or a low gain mode. When in the high gain mode, the maximum output voltage of 3.83V corresponds to a peak current of 6.667 mA. When in the high gain mode, the maximum output voltage of 3.83V corresponds to a peak current of 11.73 mA.

In example detection operations, the microprocessor is to set the detection arrangement to operate in the high gain mode. The microprocessor will then send a detection signal to the input of the detection arrangement and will first detect and determine the peak current magnitude and then determine the next decision steps in order to provide information or decision on whether there is possible human contact at the test port, which is a bare contact surface.

Referring to FIGS. 3B1 and 3B2 which are flow charts depicting example operation flows of the example detection arrangement.

In an example first scenario, if the output signal level at point 1 is smaller than 1V, the microprocessor will proceed to determine whether the signal level at collection time point 1 is at or above 0.45V, whether the signal level at collection time point 2 is larger than 0.06V, whether the signal level at collection time point 3 is between 0.4V and 0.07V (signifying a rapid fall) and whether the signal level at collection time point 4 is larger than 0.02V (non-zero). If the aforesaid conditions are all met, the microprocessor will determine that there is possible human contact at the test port.

In an example second scenario, if the output signal level at point 1 is between 1V and 2V, the microprocessor will proceed to determine whether the signal level at collection time point 3 is smaller than 0.8V (signifying a more than 50% fall in 3 μs) and whether the signal level at collection time point 4 is larger than 0.5V (non-zero). If the aforesaid conditions are all met, the microprocessor will determine that there is possible human contact at the test port.

In an example third scenario, if the output signal level at point 1 is between 2V and 3.81V, the microprocessor will proceed to determine whether the signal level at collection time point 3 is larger than 1.4V (signifying a ~50% fall in 3 μs) and whether the signal level at collection time point 4 is larger than 0.8V (non-zero). If the aforesaid conditions are all met, the microprocessor will determine that there is possible human contact at the test port.

In an example fourth scenario, if the output signal level at point 1 is larger than 3.83V, the microprocessor will switch the detection arrangement to the low gain mode and proceed to determine whether the signal level at collection time point 2 is smaller than 2V, whether the signal level at collection time point 3 is between 0.7V and 0.2V (signifying a rapid fall), whether the signal level at collection time point 4 is between 0.1V and 0.01V and whether the signal level at collection time point 5 is smaller than 0.05V. If the aforesaid conditions are all met, the microprocessor will determine that there is possible human contact at the test port.

In an example fifth scenario, if the output signal level at point 1 is larger than 3.83V, the microprocessor will switch the detection arrangement to the low gain mode and proceed to determine whether the signal level at collection time point 2 is larger than 2V, whether the signal level at collection time point 3 is between 1.7V and 0.32V, whether the signal level at collection time point 4 is between 0.01V and 0.4V, and whether the signal level at collection time point 5 is smaller than 0.25V. If the aforesaid conditions are all met, the microprocessor will determine that there is possible human contact at the test port.

In an example sixth scenario, if the output signal level at point 1 is larger than 3.83V, the microprocessor will switch the detection arrangement to the low gain mode and proceed to determine whether the signal level at collection time point 2 is larger than 3.83V, whether the signal level at collection time point 3 is smaller than 3.79V, whether the signal level at collection time point 4 is smaller than 2.0V, and whether the signal level at collection time point 5 is smaller than 1.9V. If the aforesaid conditions are all met, the microprocessor will determine that there is possible human contact at the test port.

In an example seventh scenario, if the output signal level at point 1 is larger than 3.83V, the microprocessor will switch the detection arrangement to the low gain mode and proceed to determine whether the signal level at collection time point 2 is larger than 3.83V, whether the signal level at collection time point 3 is larger than 3.83V, whether the signal level at collection time point 4 is larger than 0.85V, and whether the signal level at collection time point 5 is between 0.1V and 1.9V. If the aforesaid conditions are all met, the microprocessor will determine that there is possible human contact at the test port.

The decision criteria and related ranges to facilitate determination by the detection arrangement of whether there is living body contact at the contact surface are set out in FIGS. 3C1 to 3C7. The decision criteria and ranges are set to define an alert region in a detection time window such that when a group of detected response signals falls within the alert region, a living body will be regarded as being in direct electrical contact with the live contact surface and the detection arrangement will be set in an alert state to prevent supply of power. The detected response signals are collected at a plurality of signal collection times which are distributed sequentially in the detection time window, as depicted in FIG. 3A2. The signal collection times are distributed at timing locations where the response signals of a living body are known to carry salient or dominant characteristics. For example, data collection point 1 is to locate at the current peak, data collection point 2 is to locate proximal to at the current peak and in a region having the most rapid rate of current fall, data collection point 3 is to locate at the region where the current fall rate is slower than that of region 2 but faster than region 4, date collection point 4 is in a region of very slow fall and data collection point 5 is in a steady state current region.

In general, the data collection times are chosen to provide information on the falling characteristics of the response signals. For example, signal magnitudes collected at the data collection points 1 and 2 can facilitate determination of whether the electrical response has a current spike and/or sharpness of spike; signal magnitudes collected at the data collection points 1, 2 and 3 or points 2, 3, 4 can facilitate determination of whether there is faster fall at between points 1 and 2 and a slower fall rate at between points 2 and 3; signal magnitudes collected at the data collection points 3, 4 and 5 can facilitate determination of whether there is zero-crossing; signal magnitudes collected at the data points 1 and 5 facilitate determination of peak current magnitude and steady current and their ratio to determine shape of the pulse, etc. Of course, more data collection points can be used to provide a fuller picture of the time-domain current and time characteristics of the electrical response from the contact surface to facilitate more accurate determination.

In general, the detection criteria and ranges can be devised with reference to the time-domain characteristics of the response signals to determine whether there is matching indicating living body contact at the contact surface on the load side.

The relatively small number of data collection points which are distributed in a detection time window having a time extent comparable to the falling time from the current peak to the steady state current facilitates expeditious determination since only relative less computation steps are required. In general, a detection time window having a time extent of more than twice the falling time from the current peak to the steady state current of an average living body. In most practical applications, a detection time window having a time extent of between two to ten times of the falling time from the current peak to the steady state current of an average living body should provide more than sufficient safety margin.

Where a detection arrangement for detection of whether there is living body contact at a contact surface has a more powerful and sophisticated controller, for example, a microprocessor having a processor speed of faster than 2 GHz, more current response data, for example, hundreds or thousands of data, can be collected within the detection window without loss of generality.

When the detection arrangement is operated by a high-speed microprocessor, the data collected can be matched with a reference response by template matching, pulse shape matching, curving fitting, deep learning or other matching methods or algorithms without loss of generality.

A detection arrangement which utilizes a plurality of the time-domain responsive characteristics of the response signals of a typical living body in combination is depicted in FIG. 4. The detection arrangement comprises a zero-crossing detector, a steady-state current measurement circuit and a peak current measurement circuit. In use, the detection arrangement is operated by a controller, and the controller, peripheral circuitry and the detection arrangement to form a load detection apparatus.

In operation, the controller is to operate the peripheral circuitry to send a probing signal to the output of the load detection apparatus and then to receive an electrical response from the output. The controller may be a microprocessor and the output of the peripheral circuitry may be connected to a bare conductive surface. The received electrical response is fed to the detection arrangement. The peak current measurement circuit will then operate to measure the peak current magnitude, the steady state current measurement circuit will then operate to measure the steady state current and the zero-crossing detector will then operate to determine whether there is zero-crossing of the responsive current. The microprocessor will determine with reference to the measurement results and outcome of determination whether there is living body contact at the output of the load detection apparatus.

For example, the controller will determine with reference to the measurement results and outcome of determination whether i) the peak current is within a range of peak currents corresponding to a range of initial resistance or internal resistance of living bodies, ii) whether the response current crosses zero, and iii) whether the ratio between the steady state current and the peak current magnitude is that of a living body.

In an example application, the probing signal has a peak-to-peak voltage of 24V. A peak current of between 10 mA and 100 mA, corresponding to a range of resistance values of between 2.4 kΩ and 240Ω, is to set an alert flag. A steady state current which is less than a prescribed percentage (say 10%) of the peak current magnitude, signifying a possible current spike, is to set an alert flag. A non-detection of zero-crossing of the responsive current, signifying a resistive load, is to set an alert flag. When the flags of all the decision criteria are set as alert flags, the load detection apparatus will set into an alert mode to correspond to likely detection of living body at the contact surface. When the load detection apparatus is in the alert mode, the controller may operate to send an alert signal to prevent supply of power or other appropriate remedies without loss of generality.

An example circuit arrangement to implement a load detection apparatus comprising the detection arrangement of FIG. 4 is shown in FIGS. 4A1, 4A2, 4B1, 4B2, 4C1 and 4C2.

Referring to FIGS. 4A1 and 4A2, the microprocessor is to transmit a probing signal to the circuit input terminal "OFF LINE OFF" for output to the resistor R58. The probing signal at R58 will appear at two exposed contact terminals comprising the detection terminal HUMAN 2 and another exposed detection terminal adjacent to the detection terminal HUMAN 2 and connected to both Q10 and Q12. The detection terminal HUMAN 2 is connected to a sample-and-hold circuit of FIGS. 4B1 and 4B2 for peak current magnitude measurement. The detection terminal HUMAN 2 is connected to a zero-crossing detection circuit of FIGS. 4C1 and 4C2.

In operation, the probing signal will appear at the detection terminals comprising the detection terminal HUMAN 2. No current will through the detection terminals comprising the detection terminal HUMAN 2 until a conductive load connects the detection terminals. When the detection terminals are connected by a conductive load, the probing signal is applied to the conductive load and the response signals from the load are collected by the detection arrangement. The controller will then operate to determine whether alert flags are set in all the detection circuits, and if so, the load detection apparatus will be set in the alert mode.

An example power switching apparatus incorporating the living body detection of the present disclosure is depicted in FIG. 5. The power switching apparatus 100 is a power safety apparatus and comprising a controller and power connection circuitry. The power connection circuitry defines a switchable power connection path connecting a source side and a load side. The power connection circuitry is switchable to operate in a first operation state or an on-state or a second operation state or an off-state. When in the ON-state, impedance between the source side and the load side is very low to permit flow of operation current through the power connection circuitry with minimal loss. When in the OFF-state, the impedance between the source side and the load side is very high to impede flow of operation current through the power connection circuitry. The controller is provided and arranged to promote safe electrical operations and to mitigate potential hazardous electrical conditions on load side, such as electrical shocks to a user.

To promote safety operations, the controller is arranged to first determine whether there is a real or reasonable likelihood of living body contact, for example, human or animal body electrical contact, on the load side and to switch the power connection circuitry from the off-state to the on-state if outcome of determination is that there is no likelihood, meaning there is no real or reasonable likelihood, of direct living body contact on the load side.

The example power switching apparatus 100 comprises a switching circuitry 110, a load monitor device 120, a probing signal source 130, a control device 140, a power connection circuitry and a power circuit 160, as depicted in FIG. 5.

The power switching apparatus 100 includes a first device side (or a source side S) which is for connection to a power source and a second device side (or a load side L) which is for connection to an electrical load. The power connection circuitry includes a first current conduction portion P1 which is connected to the first device side S, a second current conduction portion P2 which is connected to the second device side L, and a power switching device SW1 which is intermediate the first P1 and the second P2 current conduction portions. The power switching device SW1 is switchable between a first operation state of very low impedance and a second operation state of very high impedance. When the power switching device SW1 is in the very low impedance first operation state (or "ON state"), a very low impedance current conduction path is established between the first device side S and the second device side L to facilitate flow of operation current between the first device side S and the second device side L. When in this ON state, the first device side S and the second device side L are operationally connected for load operation, and operational load current will flow through the power switching apparatus 100. When the power switching device SW1 is in the very high impedance second operation state (or "OFF state"), there is a very high impedance between the first device side S and the second device side L. When in this OFF state, the first device side S and the second device side L are operationally disconnected, flow of operational load current between the first device side S and the second device side L will be impeded. Where there is a current flow across the power switching apparatus 100 during this OFF-state, the current will be limited by the very high OFF-state impedance of the power switching device SW1 and the current will be limited to a non-operational load current which is negligible and/or below a safety limit. An operational load current herein means a current of a magnitude which is intended or designated for a specific or designated load. For an electrical load, the operational load current may be the rated current or rated operation current of the load. The term "ON state" is interchangeably used with the terms "ON-state", "on state", "on-state", "closed state" and the term "OFF state" is interchangeably used with the terms "OFF-state", "off state", "off-state" or "open state" herein.

The probing signal source 130 is for generating probing signals. The probing signal source 130 is operable to generate probing signals and is connected to the load side L by a probing signal switch SW2. The probing signal switch SW2 is switchable between a low impedance ON-state and a high impedance OFF-state. When the probing signal switch SW2 is closed, the probing signal switch SW2 is in the ON-state and probing signals generated by the probing signal source will flow to the load side L. When the probing signal switch SW2 is opened, the probing signal switch SW2 is in the OFF-state and probing signals generated by the probing signal source will not flow to the load side L.

The load monitor device 120 comprises a living body detection arrangement as described herein which is arranged to collect responsive electrical signals, in particular responsive signals, coming from the load side L. The detection circuitry may comprise signal processing circuitry such as shaping circuitry, amplification circuitry, filtering circuitry and other useful circuitry to process electrical signals collected from the load side L for subsequent output. In some embodiments, the detection circuitry may comprise decision circuitry to provide a decision output or a plurality of decision outputs upon receiving signals from the signal processing circuitry. In some embodiments, the detection circuitry comprises devices for collecting responsive signals on the load side. A responsive signal is one which is generated in response to a probing signal.

In typical applications, the power safety device 100 is connected to a power supply or a power source, with the first device side S connected to a power supply such as AC mains and the second device side L connected to a load, as depicted in FIG. 6. Therefore, the first device side S is also conveniently called 'source side' and the second device side L called "load side" herein. The load can be any electrical powered apparatus, appliance or tools. In some example, the power safety device 100 may be operated by a power source which is independent of the source side power supply.

In use, the power safety device 100 is initially set to be in a stand-by mode. The power safety device 100 will be subsequently set into a power operation mode when conditions on the load side L are found or determined to correspond to safe operation conditions. A condition of safe operation herein includes a condition of no direct bodily contact of a human body or an animal body with the load side. This is also a condition which is safe to a human user, a human bystander or animals in proximity so that there is no real risk or there is only minimal risk of a user encountering injury causing electrical shock such as ventricular fibrillation during load operations.

When in the standby mode, no current exceeding a safety threshold in time and in current is allowed to flow through the power safety device 100 from the source side S to the load side L. To facilitate this, the power switching device SW1 is set into the OFF state when in the stand-by mode, and only to be switched into the operational mode subsequently after satisfactory determination of safe operation conditions on the load side. When in the power operation mode, normal operational current exceeding the safety threshold time and current will be allowed to flow from the source side S to the load side L, and through the power safety device 100. To facilitate this operation to allow flow of operational currents, the power switching device SW1 is set into the ON state when in the power operation mode.

In typical or example configurations, the power safety device 100 is set into the standby mode each time when the power safety device 100 is connected to an active power source and will remain in the standby mode until actuated to operate in the operational mode.

In typical or example configurations, the power safety device 100 is reset into the standby mode after each use or completion of a cycle of power operation. A cycle of power operation means an operation current has flowed through the power safety device 100 for a minimum operation duration and followed by a period of no operation current flow exceeding a predetermined threshold pausing period. An example threshold pausing period may be set to a few second or a few minutes.

When in the standby mode, the control device 140 will operate in a pre-power operation mode. During the pre-power operation mode, load side L electrical conditions are monitored and evaluated to determine whether the load side is in a safe operation condition. When in this pre-power operation mode, the control device 140 will operate to collect electrical signals from the load side and determine whether the collected electrical signals represent safe electrical conditions on the load side. The pre-power operation is also referred herein as a pre-actuation mode or a monitoring mode.

In example monitoring mode operations, the control device 140 will operate to compare the collected electrical signals with respect to reference electrical signals or reference electrical parameters to determine whether electrical properties on the load side correspond to electrical properties of safety operations. Safe electrical conditions or electrical properties of safety operations herein include a condition of no low impedance path between a human user and the load side which would give rise to a hazardous electrical shock once the load side is connected to the source side.

In example or typical monitoring operations, the power switching device SW1 is in the OFF state, the probing signal switch SW2 is in the ON state and probing signals generated by the probing signal source will be transmitted to the load side as probing signals and to the control device 140 as reference signals. The control device 140 on evaluating the collected probing signal and upon comparison with or with respect to the reference signals would be able to determine whether electrical properties on the load side correspond to electrical properties of safety operations.

In an example monitoring mode operation flow, as depicted in FIG. 5A, the control devices 140 is at an initial state or a reset state and operates to cause sending probing signals to the load side. The control devices 140 then operates to evaluate responsive signals collected from the load side and determine whether the load side is in a safe operation condition by reference to the responsive signals and/or the probing signals. If the load side is safe for operation, the control devices 140 will proceed to operate in the next control mode. The next control mode may be a power operation mode, a mode of further checking, and/or a mode of further evaluation. If the load side is not safe for operation, the control devices 140 will return to the initial or reset state of no operation power supply to the load side.

While the power circuit 160 is connected to the source side S to obtain mains power supply for operation when in use, the power safety device 100 may be DC operated, for example, by battery operation. Where the power safety device 100 is DC operated, the power circuit may include DC-DC converters and/or DC-AC converters. In some applications, the power safety device 100 may be dually both battery and mains operated without loss of generality.

An example power switching apparatus 100 incorporating the load detection apparatus of FIG. 4 is depicted in FIG. 5B as an example.

The above are just example directions to facilitate determination of living body presence at the load side. Other characteristic features of the responsive current typical of a living body disclosed herein can of course be used without loss of generality.

While example application and utilization of the various observations and phenomenon have been described with examples herein, it should be appreciated that other applications and utilizations are possible without loss of generality and the example applications and utilizations are intended to provide non-limiting examples.

The invention claimed is:

1. An electronic circuit arrangement for detection of electrical contact of a living body with a contact surface, wherein the living body has electrical characteristics resembling an impedance network comprising a first impedance portion, a second impedance portion and a third impedance portion connected in series; wherein the first impedance portion comprises a first capacitor of a first capacitance value and a first resistor of a first resistance value connected in parallel to form a first impedance bridge, the second impedance portion comprises a second capacitor of a second capacitance value and a second resistor of a second resistance value connected in parallel to form a second impedance bridge, and the third impedance portion comprises a third capacitor of a third capacitance value and a third resistor of a third resistance value connected in parallel to form a third impedance bridge; and wherein the impedance network has a characteristic charge rise-time and a characteristic discharge fall-time;

wherein the electronic circuit arrangement comprises a solid-state controller, a non-volatile data storage device, a probing signal source and a responsive signal collector:

wherein the signal source is to generate a probing pulse or a train of probing pulses as a probing signal, and to transmit the probing signal to contact terminals;

wherein the responsive signal collector is for collecting a responsive signal at the contact terminals, the responsive signals being signals generated in response to or in reaction to the probing signal acting on the contact terminals;

wherein the probing pulse comprises a probing pulse base state at a probing pulse base state voltage, a probing state at a probing state voltage and a probing pulse intermediate state having intermediate voltages;

wherein the probing pulse rises from the probing pulse base state voltage to the probing state voltage in a rise-time which is a probing pulse rise time, stays in the probing state for a duration which defines a probing state duration, returns to the probing pulse base state at the end of the probing state, and stays in the probing pulse base state for a probing base state duration until end of the probing pulse;

wherein the intermediate voltages of the probing pulse intermediate state increase with time when the probing pulse changes from the probing pulse base state to the probing state;

wherein the probing pulse and the impedance network are related or characterized such that when the probing pulse is applied on the impedance network, an expected response pulse comprising an expected pulse base state having an expected pulse base magnitude and pertinent electrical characteristics is expected, wherein the pertinent electrical characteristics comprises an expected pulse peak, an expected pulse steady state and an expected pulse transition state interconnecting the expected pulse peak and the expected pulse steady state; wherein the expected pulse peak has an expected pulse signal magnitude, the expected pulse peak signal magnitude being an electrical parameter bearing or having a correlation between the probing state voltage and the second resistance value; wherein the expected pulse steady state has an expected steady state signal magnitude, the steady state signal magnitude bearing or having a correlation between the probing state voltage and sum of resistance values of the resistors of the impedance network; and the expected pulse transition state has a fall time or fall-time characteristics commensurate with or corresponding to the characteristic discharge fall-time of the impedance network;

and wherein the controller is to capture a plurality of electrical parameters of the responsive signal at a plurality of capture times, to determine with reference to the captured electrical parameters whether the responsive signal comprises a response pulse having the pertinent electrical characteristics of or corresponding to the expected response pulse, and to send out a control signal indicative of positive living body detection upon a positive outcome of determination.

2. The electronic circuit arrangement according to claim 1, wherein the probing pulse is configured such that the expected pulse peak is a single dominant peak of the expected response pulse and having an expected peak magnitude of a first electrical polarity, wherein the steady state signal magnitude of the expected pulse steady state has a non-zero magnitude and the first electrical polarity, and wherein the expected response pulse is a non-zero-crossing pulse.

3. The electronic circuit arrangement according to claim 1, wherein the probing pulse is configured such that the expected steady state signal magnitude is intermediate the expected pulse peak signal magnitude and the expected pulse base magnitude, and wherein the expected steady state signal magnitude, the expected pulse peak signal magnitude and the expected pulse base magnitude have same electrical polarity which is a first electrical polarity.

4. The electronic circuit arrangement according to claim 1, wherein the probing pulse is configured such that the expected response pulse rises from the expected pulse base to the expected pulse peak in an expected pulse rise time, and wherein the expected pulse rise time is equal to or slightly larger than the probing pulse rise time.

5. The electronic circuit arrangement according to claim 1, wherein the probing pulse is configured such that the expected response pulse falls from the expected pulse peak to the expected pulse steady state in an expected pulse fall time, and wherein the expected pulse fall time is equal to or shorter than the probing state duration of the probing pulse.

6. The electronic circuit arrangement according to claim 1, wherein the probing pulse is configured such that the expected response pulse begins to fall from the expected pulse steady state towards the expected pulse base state at a time when the probing pulses falls from the probing state to the probing pulse base state, and wherein the expected response pulse reaches the expected pulse base state during the probing pulse base state of a probing pulse.

7. The electronic circuit arrangement according to claim 1, wherein the probing pulse is configured such that the expected response pulse has a rising side and a rising portion and a falling side and a falling portion, wherein the rising side and the falling side are divided by the expected pulse peak, and the rising portion and the falling portion are interconnected by the expected pulse peak; wherein the rising portion has a rising portion duration and the falling portion has a falling portion duration, wherein the rising portion is a thin portion and the falling portion is a slowly flaring fat portion, and wherein the falling portion duration is significantly longer than the rising portion duration.

8. The electronic circuit arrangement according to claim 7, wherein the expected pulse transition state and the expected pulse steady state are on the falling side and occur sequentially after the expected response pulse has risen to the expected pulse peak; wherein the expected pulse transition state has a first falling portion and a second falling portion, and wherein the first and second falling portions cooperate to form a concavely curved falling side; and wherein the controller is to determine with reference to the captured electrical characteristics of the responsive signal whether the response signal is a responsive pulse having a concavely curved falling side, and to send out a control signal indicative of positive living body detection upon a positive outcome of determination.

9. The electronic circuit arrangement according to claim 8, wherein the first falling portion is a rapidly falling falling-portion which continues immediately from the expected pulse peak, and the second falling portion is a slower falling falling-portion which ends to join the expected pulse steady state.

10. The electronic circuit arrangement according to claim 8, wherein the first falling portion falls at a rate resembling a free-fall relative to the second falling portion, and the second falling portion falls following an asymptotic manner.

11. The electronic circuit arrangement according to claim 1, wherein the probing pulse rise-time is set to facilitate capture of the expected pulse peak magnitude, and the probing pulse rise-time is set to correspond to be comparable to a minimum sample-and-hold time requirement of an integrated circuit fast sample-and-hold circuit.

12. The electronic circuit arrangement according to claim 1, wherein the probing pulse has a probing pulse rise-time of up to 1.5 μs, including between 300 ns and 1.5 ms.

13. The electronic circuit arrangement according to claim 1, wherein the probing pulse has a linear rising edge or a non-linear rising edge, the rising edge having a monotonous rising edge.

14. The electronic circuit arrangement according to claim 1, wherein the controller is configured to operate to capture a signal magnitude of the responsive signal at a capture time immediately after the probing pulse has risen from the probing pulse base state to the probing state.

15. The electronic circuit arrangement according to claim 1, wherein the controller is configured to operate to capture a plurality of signal magnitudes of the responsive signal during the expected pulse transition state, and a plurality of signal magnitude samples of the responsive signal during the expected pulse steady state.

16. The electronic circuit arrangement according to claim 1, wherein the electronic circuit arrangement comprises a pulse broadening circuit to spread the expected pulse peak to a more rounded peak to facilitate measurement of the expected pulse peak magnitude.

17. A method of detecting possible living body contact at a contact surface, wherein the method comprises a controller sending a probing signal and detecting current parameters of a responsive signal to determine whether there is possible living body contact at the contact surface, wherein the probing signal comprises a probing pulse or a train of probing pulses, the probing pulse comprising a probing pulse base state at a probing pulse base state voltage, a probing state at a probing state voltage, and a probing pulse intermediate state having intermediate voltages;

wherein the probing pulse rises from the base state voltage to the probing state voltage in a rise-time which is a probing pulse rise time, stays in the probing pulse probate state for a duration which defines a probing state duration, returns to the probing pulse base state at the end of the probing state, and stays in the probing pulse base state for a probing base state duration until end of the probing pulse;

wherein the probing pulse is configured such that the responsive pulse comprises a rising side, a flared falling side, a non-zero steady state current on the falling side, and a current spike defined by cooperation of the rising side and falling side and having a peak current magnitude, and wherein the method comprises broadening the current spike to facilitate capture of the peak current magnitude.

18. The method of claim 17, wherein the probing pulse has a rise time of between 200 ns and 1.5 μS, and the responsive pulse has a fall time which is more than 20 times the rise time.

19. The method of claim 17, wherein the method comprises using a probing pulse having a rise time of below 200 ns and using an operational amplifier to broaden the current spike to facilitate capture of the peak current magnitude.

20. The method of claim 17, wherein the method comprises using a probing pulse having a rise time such that the current spike of the responsive pulse has a rounded peak.

* * * * *